(12) United States Patent
Takahashi et al.

(10) Patent No.: US 7,547,514 B2
(45) Date of Patent: Jun. 16, 2009

(54) METHODS FOR MONITORING GENOMIC DNA OF ORGANISMS

(75) Inventors: Toru Takahashi, Tokyo (JP); Deborah John Boles, Sterling, VA (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 238 days.

(21) Appl. No.: 11/190,942

(22) Filed: Jul. 28, 2005

(65) Prior Publication Data

US 2006/0115830 A1  Jun. 1, 2006

Related U.S. Application Data

(60) Provisional application No. 60/591,596, filed on Jul. 28, 2004.

(51) Int. Cl.
 *C12Q 1/68* (2006.01)
 *C12P 19/34* (2006.01)
(52) U.S. Cl. .......................................... 435/6; 435/91.2
(58) Field of Classification Search ...................... None
 See application file for complete search history.

(56) References Cited

U.S. PATENT DOCUMENTS

| | | | |
|---|---|---|---|
| 5,779,868 A | 7/1998 | Parce et al. | 204/604 |
| 5,800,690 A | 9/1998 | Chow et al. | 204/451 |
| 5,876,675 A | 3/1999 | Kennedy | 422/99 |
| 5,882,465 A | 3/1999 | McReynolds | 156/285 |
| 5,965,410 A | 10/1999 | Chow et al. | 435/91.2 |
| 6,174,709 B1 * | 1/2001 | Kenten et al. | 435/91.2 |
| 6,267,858 B1 | 7/2001 | Parce et al. | 204/600 |
| 6,337,212 B1 | 1/2002 | Nagle et al. | 436/174 |
| 6,379,974 B1 | 4/2002 | Parce et al. | 436/180 |
| 6,416,642 B1 | 7/2002 | Alajoki et al. | 204/451 |
| 6,465,257 B1 | 10/2002 | Parce et al. | 436/180 |
| 6,482,364 B2 | 11/2002 | Parce et al. | 422/100 |
| 6,495,369 B1 | 12/2002 | Kercso et al. | 436/47 |
| 6,500,323 B1 | 12/2002 | Chow et al. | 204/450 |
| 6,534,262 B1 | 3/2003 | McKernan et al. | 435/6 |
| 6,556,923 B2 | 4/2003 | Gallagher et al. | 702/23 |
| 6,558,944 B1 | 5/2003 | Parce et al. | 435/287.2 |
| 6,558,960 B1 | 5/2003 | Parce et al. | 436/519 |
| 6,582,576 B1 | 6/2003 | Chow et al. | 204/601 |
| 6,613,581 B1 | 9/2003 | Wada et al. | 436/518 |
| 6,670,153 B2 | 12/2003 | Stern | 435/91.2 |
| 6,718,742 B1 | 4/2004 | Baker | 54/28 |
| 6,752,966 B1 | 6/2004 | Chazan | 422/102 |
| 6,852,524 B2 | 2/2005 | Okamura et al. | 435/287.1 |
| 2003/0054395 A1 | 3/2003 | Baker | 435/6 |
| 2003/0104466 A1 | 6/2003 | Knapp et al. | 435/6 |
| 2003/0130499 A1 | 7/2003 | Baker | 536/25.4 |
| 2004/0089548 A1 | 5/2004 | Burd Mehta et al. | 204/450 |
| 2004/0152076 A1 | 8/2004 | Willson et al. | 435/6 |
| 2004/0241651 A1 * | 12/2004 | Olek et al. | 435/6 |
| 2005/0009022 A1 | 1/2005 | Weiner et al. | 435/6 |

FOREIGN PATENT DOCUMENTS

| | | |
|---|---|---|
| EP | 1149921 A | 10/2001 |
| EP | 1 510 576 A1 | 3/2005 |
| JP | 2002-291500 | 10/2002 |
| JP | 2002-325581 | 11/2002 |
| JP | 2003-083965 | 3/2003 |
| JP | 2003-093075 | 4/2003 |
| JP | 2003-180351 | 7/2003 |
| JP | 2003-180374 | 7/2003 |
| JP | 2003-274959 | 9/2003 |
| JP | 2003-334082 | 11/2003 |
| JP | 2004-041191 | 2/2004 |
| JP | 2004-057202 A | 2/2004 |
| JP | 2004-185583 | 7/2004 |
| JP | 2004-236651 | 8/2004 |
| JP | 2004-361310 A | 12/2004 |
| WO | WO 94/24307 A | 10/1994 |
| WO | WO 97/41219 | 11/1997 |
| WO | WO 99/12031 A | 3/1999 |
| WO | WO 99/16162 | 4/1999 |
| WO | WO 01/02850 A | 1/2001 |
| WO | WO 02/10373 A2 | 2/2002 |
| WO | WO 02/083952 A | 10/2002 |
| WO | WO 2004/090132 | 10/2004 |

(Continued)

OTHER PUBLICATIONS

Kong et al. Rapid-cycle PCR for detection and typing of *Mycoplasma pneumoniae* in clinical specimens. J. Clin. Microbiol. (2000) vol. 38, No. 2, pp. 4256-4259.*

(Continued)

*Primary Examiner*—Kenneth R. Horlick
*Assistant Examiner*—David C Thomas
(74) *Attorney, Agent, or Firm*—Rothwell, Figg, Ernst & Manbeck

(57) ABSTRACT

The invention provides novel SGP primers for improved use in waveform-profiling methods of DNA amplification. In one embodiment, use of an SGP primer in a method of DNA amplification results in exponential amplification of several distinct products. In another embodiment, the methods of the invention further comprise a novel half-time elongation step. In another embodiment, the distinct products may be detected via melting temperature analysis. The primers and methods of the invention may be combined to determine an organism in a sample.

19 Claims, 11 Drawing Sheets

FOREIGN PATENT DOCUMENTS

| WO | WO 2004/104196 | 12/2004 |
|----|----------------|---------|
| WO | WO 2005/003395 | 1/2005  |
| WO | WO 2005/005664 | 1/2005  |

OTHER PUBLICATIONS

Adgene Co., Ltd. "Goodbye DNA Chip, Hello Genopattern for 21$^{st}$ Century" (www.adgene.co.jp) (published at least as early as Nov. 24, 2002; pp. 1-8).

Adgene Co., Ltd. "A method for comparison and identification of DNAs and RNAs by pattern analysis: Genopattern Method" (www.adgene.co.jp) (published at least as early as Nov. 24, 2002; pp. 1-9).

Alberti and Mergny "DNA duplex-quadruplex exchange as the basis for a nanomolecular machine" *PNAS* 100(4):1569-73 (Feb. 2003).

Antolin et al. "Intensive Linkage Mapping in a Wasp (*Bracon hebetor*) and a Mosquito (*Aedes aegypti*) with Single-Strand Conformation Polymorphism Analysis of Random Amplified Polymorphic DNA Markers" *Genetics* 143:1727-38 (Aug. 1996).

Arnau et al. "The Use of RAPD Markers in the Genetic Analysis of the Plant Pathogenic Fungus *Cladosporium fulvum*" *Curr. Genet.* 25:438-44 (1994).

Butler "Nucleic acid sequence analysis software packages" *Curr. Opin. Biotechnol.* 5(1):19-23 (1994).

Burpo "A critical review of PCR primer design algorithms and cross-hybridization case study" Standford Computer Molecular Biology Course Materials (2001) (cmgm.stanford.edu/biochem218/Projects%202001/Burpo.pdf) (printed Apr. 12, 2007; pp. 1-11).

Cooksey et al. "Temperature-Mediated Heteroduplex Analysis Performed by Using Denaturing High-Performance Liquid Chromatography To Identify Sequence Polymorphisms in *Mycobacterium tuberculosis* Complex Organisms" *J. Clin. Microbiol.* 40:1610-16 (May 2002).

Constans "Nano-Quakes: Advalytix's programmable biochips shake up the lab-on-a-chip market" *The Scientist* 17(7):48 (Apr. 2003). (www.the-scientist.com/yr2003/apr/tools_030407.html) (printed Mar. 18, 2004; pp. 1-3).

Darby et al. "High throughput measurement of duplex, triplex and quadruplex melting curves using molecular beacons and a LightCycler" *Nucleic Acids Res.* 30(9):e39, 1-8 (May 2002).

Descheemaeker et al. "Evaluation of Arbitrarily Primed PCR Analysis and Pulsed-Field Gel Electrophoresis of Large Genomic DNA Fragments for Identification of Enterocci Important in Human Medicine" *Int. J. Syst. Bacteriol.* 47(2):555-61 (Apr. 1997).

Holding "Lab on a Chip: Miniaturized microfluidic device analyzes multiple samples in parallel" *The Scientist* (Mar. 15, 2004) (www.biomedcentral.com/news/20040315/02) (printed Mar. 18, 2004; pp. 1-3).

Kemp "Capillary electrophoresis: a versatile family of analytical techniques" *Biotechnol. Appl. Biochem.* 27:9-17 (Feb. 1998).

Kopp et al. "Chemical amplification: continuous-flow PCR on a chip" *Science* 280:1046-48 (May 1998).

Kozwich et al. "Development of a Novel, Rapid Integrated *Crptosporidium parvum* Detection Assay" *Appl. Environ. Microbiol.* 66(7):2711-17 (Jul. 2000).

Marx "PCR-on-a-Chip Downsizes Even as It Grows Up" *Genomics & Proteomics* (www.genpromag.com/ShowPR_Print.aspx?PUBCODE=018&ACCT~1800000100~ISSUE~0404~RELTYPE~PR~ORIGRELTYPE~GPF~PRODCODE~( (printed Jun. 7, 2007; pp. 1-4).

Naimuddin et al. "Commonly Conserved Genetic Fragments Revealed by Genome Profiling Can Serve as Tracers of Evolution" *Nucleic Acids Res.* 30(10):e42, 1-6 (May 2002).

"Melting Curve Technology" (Roche Diagnostics Corporation (2003)) (www.roche-applied-science.com/sis/lighttyper/lt_frames/frame_technology.jsp) (printed Jun. 6, 2007; pp. 1-2).

Schwartz et al. "Detection of antibiotic-resistant bacteria and their resistance genes in wastewater, surface water, and drinking water biofilms," *FEMS Microbiol. Ecol.* 43:325-35 (2003) (first published online Nov. 23, 2002).

Sinclair "Small Wonder: Agilent Technologies and Caliper Technologies bring lab-on-a-chip technology to the research bench" *The Scientist* 14(5):25-27 (Mar. 2000) (www.the-scientist.com/yr2000/mar/profile_000306.html) (printed Mar. 18, 2004; pp. 1-3).

Swaminathan and Barrett "Amplification Methods for Epidemiologic Investigations of Infectious Diseases" *J. Microbiol. Meth.* 23:129-39 (1995).

Wang et al. "RAPD (Arbitrary Primer) PCR is More Sensitive than Multilocus Enzyme Electrophoresis for Distinguishing Related Bacterial Strains" *Nucleic Acids Res.* 21(25):5930-33 (1993).

Welsh and McClelland "Fingerprinting Genomes Using PCR With Arbitrary Primers" *Nucleic Acids Res.* 18(24):7213-18 (Dec. 1990).

Williams et al. "DNA polymorphisms amplified by arbitrary primers are useful as genetic markers" *Nucleic Acids Res.* 18(22):6531-34 (Oct. 1990).

"Geopattern Analyzer GP1000" (www.yamato-net.co.jp/english/products/bio/gp1000.htm) (printed May 21, 2007; pp. 1-8).

"PCR Primer Design" (www.premierbiosoft.com/tech_notes/PCR_Primer_Design.html) (printed Apr. 12, 2007; pp. 1-5).

* cited by examiner

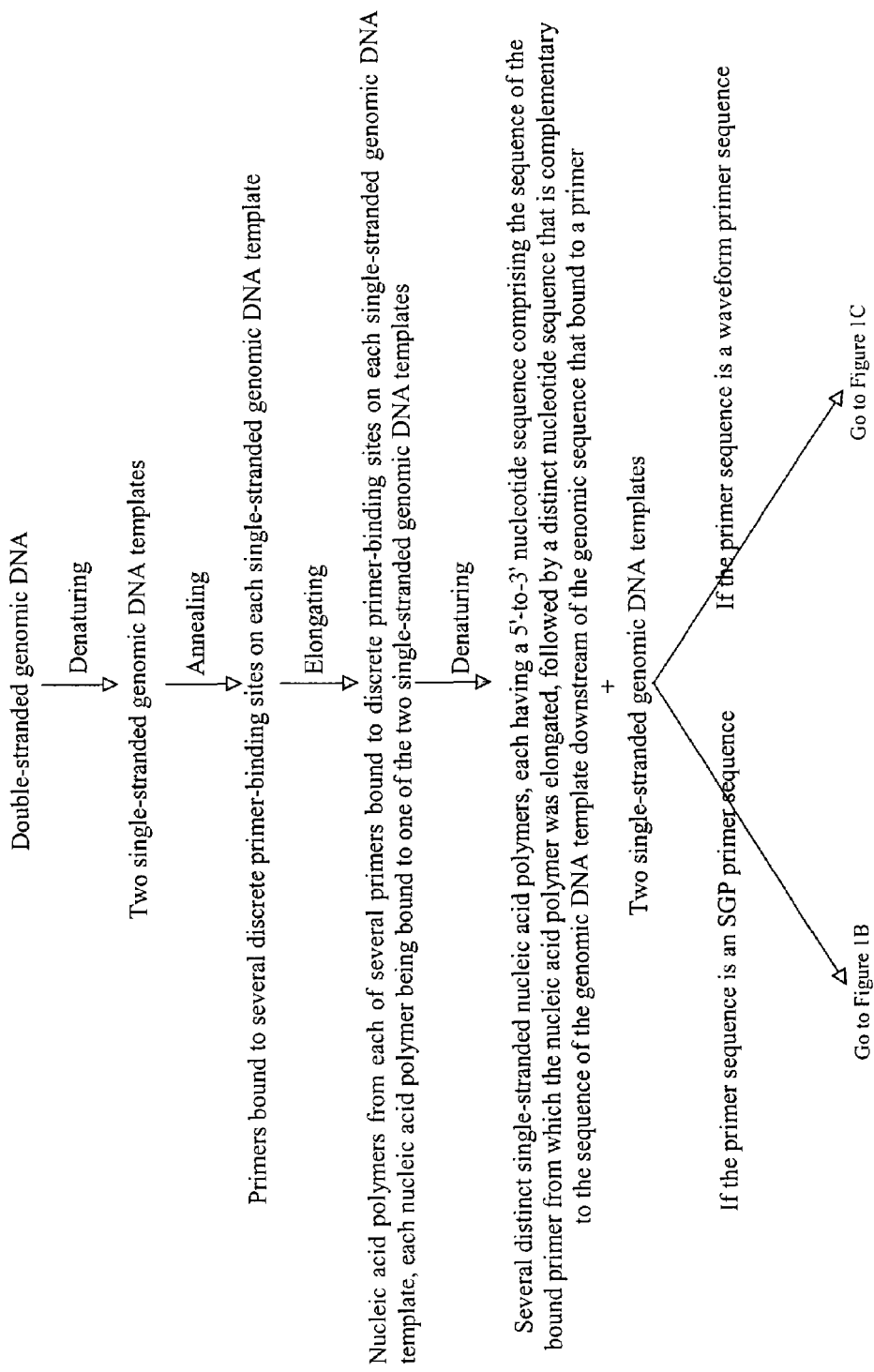

5' TCTTGCACTTTGGGTAACGCACGTGTGGCTGCGCTTCAAGTCATACCGCGAAC 3'
3' agaacgtgaaacccattgcgtgcacaccgacgcgaagttcagtatggcgcttg 5'

5' TATTATGCGCAGCCGACAGCAACTATCTGAACGAGCGAGGGCCATCAAGCCTG 3'
3' ataatacgcgtcggctgtcgttgatagacttgctcgctcccggtagttcggac 5'

5' GCATATCGTCAGGTCACCACGTGGGTGCAATGCGCGTCACTCTCTTCCACCCT 3'
3' cgtatagcagtccagtggtgcacccacgttacgcgcagtgagagaaggtggga 5'

5' TGTGTAATAATTGTACAAACATCCACTGTTCTCTCAGAGAACATATGTCCCCG 3'
3' acacattattaacatgtttgtaggtgacaagagagtctcttgtatacaggggc 5'

5' GCGCTCTAAGTAACACCGGCAAAATTTTTGAAGCCCAAAGGGCCTTCGGCTGC 3'
3' cgcgagattcattgtggccgttttaaaaactcgggtttcccggaagccgcg 5'

5' CAACTCTCGGAGGATCGCCGTTCAACCGCCGGTAGAGACAGTATACAAATTAT 3'
3' gttgagagcctcctagcggcaagttggcggccatctctgtcatatgtttaata 5'

5' ACAGAGTCCTATGGCAGGATTGTTCTCCAGTATGCAACCGTGAGGCACGCCAG 3'
3' tgtctcaggataccgtcctaacaagaggtcatacgttggcactccgtgcggtc 5'

5' AAGCAGTCTGTCTTTCCTGGGACGTGAATTTGCTTTGATTGCATGCTCAGTAC 3'
3' ttcgtcagacagaaaggaccctgcacttaaacgaaactaacgtacgagtcatg 5'

5' GCGAGGCTTCTCCGCAAGATTCACAAAAGCAACGCGGTTTGCCAACGTAGGGA 3'
3' cgctccgaagaggcgttctaagtgttttcgttgcgccaaacggttgcatccct 5'

5' TTGAGACCAAATCCCATCGGTAATTGAGGCAAAGATTCCGCCAGCCATGGTAA 3'
3' aactctggtttagggtagccattaactccgtttctaaggcggtcggtaccatt 5'

5' ATTACCCTTCTACCTGGGAAGCTAGCGATTGCGTGGACAAAGCGCATGTGCGA 3'
3' taatgggaagatggaccctcggtcgctaacgcacctgtttcgcgtacacgct 5'

5' GCGGACGTTGGGCAGTCCAGAAAGAGGTAGCGGGGGCTATCTATTAGTAACGA 3'
3' cgcctgcaacccgtcaggtctttctcctcgccccgatagataatcattgct 5'

5' CATAGGAGGTCCGAGATAGGTACCCAATTTCTTTATATTGTTAGGGATTCCCC 3'
3' gtatcctccaggctctatccatgggttaaagaaatataacaatccctaagggg 5'

5' GTACTCTCCTTTCAGGGGCCTAAGGACCCTTTCTTCCGACGTTTACTATACCT 3'
3' catgagaggaaagtccccggattcctgggaagaaggctgcaaatgatatgga 5'

5' AGCATGGTCTTAAGGGATCCATTTATCTGTATGTAGTATTACGTTGGTGCTGA 3'
3' tcgtaccagaattccctaggtaaatagacatacatcataatgcaaccacgact 5'

5' TCAGTTTATACTCCGCTGTGACCATCGTTAAGTATACCACCGGCTAACTCCGC 3'
3' agtcaaatatgaggcgacactggtagcaattcatatggtggccgattgaggcg 5'

5' GCTTATGGGGACTTATGGCTTCATGGCCCACTTACAAGATGGGTGAGTTCGT 3'
3' cgaataccccctgaataccgaagtaccgggtgaatgttctacccactcaagca 5'

5' GTTCCACCACCTGTCCGGGGTGCTGAGGCAGATGTGATCGTTGGTAGGCCCAA 3'
3' caaggtggtggacaggccccacgactccgtctacactagcaaccatccgggtt 5'

5' GTTCAGCCGATGATGCCTTGCTCCTCGCAGTAGATGCAGCACTCTTC 3'
3' caadtcggctactacggaacgaggagcgtcatctacgtcgtgagaag 5'

FIGURE 2

SEQ ID NO:2

3' agaacgtgaaaccattgcgtgtgcacaccgacgcgaagttcagtatggcgcttgataatacgcgtcggctgtcgttgatagacttgctcgctccc 5'
                                                                              agc →  agc
3' ggtagttcggaccgtatagcagtccagtggtgcacccacgttacgcgcagtgagagaaggtgggaacacattattaacatgtttgtaggtgaca 5'
        agc
3' agagagtctcttgtatacaggggccgcgagattcattgtggccgtttaaaaacttcgggtttcccgaagccgacggttgagagcctcctagc 5'
                                                        agc
3' ggcaagttggcgcggccatctctgtcatatgtttaatatgtctcaggatacaagaggtcatacgttggcactccgtgcggtcttcgt 5'
                                                                                      agc
3' cagacagaaaggaccctgcacttaaacgaaactaacgtacgagtcatgctcctccgaagagagcgttctaagtgttttcgttgcgccaaacgttg 5'
                                                                              agc
3' catccctaactctggtttaggggtagccattaactccgtttctaaggcggtcggtaccatttaatgggaagatggaccctcgatcgctaacgca 5'
                                                                              agc   agc
3' cctgtttcgcgtacacgctcgcctgcaaccgtcaggtctttctcctccatcgccccgatagataatcattgctgtatcctccaggctctatccat 5'
        agc                                        agc
3' gggttaaagaataataacaatccctaagggcatgagagaaagtcccggattcctgggaaagaaggctgcaaatgatatggatcgtaccaga 5'
                                                                                        agc
3' attccctaggtaaatagacatacatcatatgcaaccgactagtcaaatatgaggcgacactggtagcaattcatatgtggcgattgagg 5'
3' cgcgaatacccctgaataccgaagtaccgggtgaatgttctaccactcaagcacaaggtgtggacaggcccacgactccgtctacactag 5'
3' caaccatccgggttcaagtcggctactacggaacgaggagcgtcatctacgcgtgagaag 5'
                                                agc

| SGP nucleic acid polymers derived from the genomic DNA template set forth as SEQ ID NO:2 | SGP nucleic acid polymers derived from the genomic DNA template set forth as SEQ ID NO:1 |
|---|---|
| 5'-AGCCGAC-3' (SEQ ID NO:3) | 3'-aacccattgcgtgcacaccga-5' (SEQ ID NO:19) |
| 5'-AGCAACTATCTGAACG-3' (SEQ ID NO:4) | 3'-cgcga-5' (SEQ ID NO:20) |
| 5'-AGCGAGGGCCATCA-3' (SEQ ID NO:5) | 3'-tcttgtatacaggggccgcga-5' (SEQ ID NO:21) |
| 5'-AGCCTGGCATATCGTCAGGTC-3' (SEQ ID NO:6) | 3'-ttcgggtttcccggaagccga-5' (SEQ ID NO:22) |
| 5'-AGCCCAAAGGGCCTTCGGCTG-3' (SEQ ID NO:7) | 3'-aaggaccctgcacttaaacga-5' (SEQ ID NO:23) |
| 5'-AGCAGTCTGTCTTTCCTGGGA-3' (SEQ ID NO:8) | 3'-aactaacgtacga-5' (SEQ ID NO:24) |
| 5'-AGCAACGCGGTTTGCCAACGT-3' (SEQ ID NO:9) | 3'-gtcatgcgctccga-5' (SEQ ID NO:25) |
| 5'-AGCCATGGTAAATTACCCTTC-3' (SEQ ID NO:10) | 3'-atgggaagatggacccctcga-5' (SEQ ID NO:26) |
| 5'-AGCT-3' (SEQ ID NO:11) | 3'-gtctttctccatcgccccga-5' (SEQ ID NO:27) |
| 5'-AGCGATTGCGTGGACAA-3' (SEQ ID NO:12) | 3'-tacatcataatgcaaccacga-5' (SEQ ID NO:28) |
| 5'-AGCGCATGTGCG-3' (SEQ ID NO:13) | 3'-ctagtcaaatatgaggcga-5' (SEQ ID NO:29) |
| 5'-AGCGGACGTTGGGCAGTCCAG-3' (SEQ ID NO:14) | 3'-agcaattcatatggtggccga-5' (SEQ ID NO:30) |
| 5'-AGCGGGGGCTATCTATTAGTA-3' (SEQ ID NO:15) | 3'-ttgaggcgcga-5' (SEQ ID NO:31) |
| 5'-AGCATGGTCTTAAGGGATCCA-3' (SEQ ID NO:16) | 3'-atacccctgaataccga-5' (SEQ ID NO:32) |
| 5'-AGCCGATGATGCCTTGCTCCT-3' (SEQ ID NO:17) | 3'-ggtggtggacaggccccacga-5' (SEQ ID NO:33) |
| 5'-AGCACTCTTC-3' (SEQ ID NO:18) | 3'-aagtcggctactacggaacga-5' (SEQ ID NO:34) |

FIGURE 5

| SGP-SGP nucleic acid polymers amplified from SGP nucleic acid polymers derived from the genomic DNA template set forth as SEQ ID NO:2 | SGP-SGP nucleic acid polymers amplified from SGP nucleic acid polymers derived from the genomic DNA template set forth as SEQ ID NO:1 |
|---|---|
| Not applicable | Not applicable |
| Not applicable | Not applicable |
| Not applicable | Not applicable |
| Not applicable | 5'-AGCCCAAAGGGCCTTCGGCT-3' (SEQ ID NO:39) |
| 3'-tcgggtttcccggaagccga-5' (SEQ ID NO:35) | Not applicable |
| Not applicable | Not applicable |
| Not applicable | Not applicable |
| Not applicable | 5'-AGCT-3' (SEQ ID NO:40) |
| 3'-tcga-5' (SEQ ID NO:36) | 5'-AGCGGGGGCT-3' (SEQ ID NO:41) |
| Not applicable | Not applicable |
| Not applicable | Not applicable |
| Not applicable | Not applicable |
| 3'-tcgcccccga-5' (SEQ ID NO:37) | Not applicable |
| Not applicable | Not applicable |
| 3'-tcggctactacggaacga-5' (SEQ ID NO:38) | Not applicable |
| Not applicable | 5'-AGCCGATGATGCCTTGCT-3' (SEQ ID NO:42) |

FIGURE 6

| Shortened SGP nucleic acid polymers (underlined) elongated from SGP-SGP nucleic acid polymers amplified from SGP nucleic acid polymers derived from the genomic DNA template set forth as SEQ ID NO:2 | Shortened SGP nucleic acid polymers (underlined) elongated from SGP-SGP nucleic acid polymers amplified from SGP nucleic acid polymers derived from the genomic DNA template set forth as SEQ ID NO:1 |
|---|---|
| Not applicable | Not applicable |
| Not applicable | Not applicable |
| Not applicable | Not applicable |
| Not applicable | 3'-cggaagccga-5' (SEQ ID NO:47) |
| 5'-AGCCCAAAGG-3' (SEQ ID NO:43) | Not applicable |
| Not applicable | Not applicable |
| Not applicable | Not applicable |
| Not applicable | 3'-tcga-5' (SEQ ID NO:48) |
| 5'-AGCT-3' (SEQ ID NO:44) | 3'-tcgccccga-5' (SEQ ID NO:49) |
| Not applicable | Not applicable |
| Not applicable | Not applicable |
| Not applicable | Not applicable |
| 5'-AGCGGGGGCT-3' (SEQ ID NO:45) | Not applicable |
| Not applicable | Not applicable |
| 5'-AGCCGATGAT-3' (SEQ ID NO:46) | Not applicable |
| Not applicable | 3'-tacggaacga-5' (SEQ ID NO:50) |

SEQUENCE LISTING

<160> NUMBER OF SEQ ID NOS: 52

<210> SEQ ID NO 1
<211> LENGTH: 1001
<212> TYPE: DNA
<213> ORGANISM: Artificial
<220> FEATURE:
<223> OTHER INFORMATION: Theoretical single-strand DNA template

<400> SEQUENCE: 1

```
tcttgcactt tgggtaacgc acgtgtggct gcgcttcaag tcataccgcg aactattatg      60
cgcagccgac agcaactatc tgaacgagcg agggccatca agcctggcat atcgtcaggt     120
caccacgtgg gtgcaatgcg cgtcactctc ttccaccctt gtgtaataat tgtacaaaca     180
tccactgttc tctcagagaa catatgtccc cggcgctcta agtaacaccg gcaaaatttt     240
tgaagcccaa agggccttcg gctgccaact ctcggaggat cgccgttcaa ccgccggtag     300
agacagtata caaattatac agagtcctat ggcaggattg ttctccagta tgcaaccgtg     360
aggcacgcca gaagcagtct gtctttcctg ggacgtgaat ttgctttgat tgcatgctca     420
gtacgcgagg cttctccgca agattcacaa aagcaacgcg gtttgccaac gtagggattg     480
agaccaaatc ccatcggtaa ttgaggcaaa gattccgcca gccatggtaa attacccttc     540
tacctgggga gctagcgatt gcgtggacaa agcgcatgtg cgagcggacg ttgggcagtc     600
cagaaagagg tagcggggc tatctattag taacgacata ggaggtccga gataggtacc     660
caatttcttt atattgttag ggattccccg tactctcctt tcaggggcct aaggacccctt     720 tcttccgacg tttactatac ctagcatggt cttaagggat ccatttatct gtatgtagta     780
ttacgttggt gctgatcagt ttatactccg ctgtgaccat cgttaagtat accaccggct     840
```

```
aactccgcgc ttatggggga cttatggctt catggcccac ttacaagatg ggtgagttcg    900
tgttccacca cctgtccggg gtgctgaggc agatgtgatc gttggtaggc ccaagttcag    960
ccgatgatgc cttgctcctc gcagtagatg cagcactctt c                       1001
```

<210> SEQ ID NO 2
<211> LENGTH: 1001
<212> TYPE: DNA
<213> ORGANISM: Artificial
<220> FEATURE:
<223> OTHER INFORMATION: Theoretical single-strand DNA template
<220> FEATURE:
<221> NAME/KEY: misc_feature
<223> OTHER INFORMATION: This sequence is in 3' to 5' direction.

<400> SEQUENCE: 2

```
agaacgtgaa acccattgcg tgcacaccga cgcgaagttc agtatggcgc ttgataatac     60
gcgtcggctg tcgttgatag acttgctcgc tcccggtagt tcggaccgta tagcagtcca    120
gtggtgcacc cacgttacgc gcagtgagag aaggtgggaa cacattatta acatgtttgt    180
aggtgacaag agagtctctt gtatacaggg gccgcgagat tcattgtggc cgttttaaaa    240
acttcgggtt tcccggaagc cgacggttga gagcctccta gcggcaagtt ggcggccatc    300
tctgtcatat gtttaatatg tctcaggata ccgtcctaac aagaggtcat acgttggcac    360
tccgtgcggt cttcgtcaga cagaaaggac cctgcactta aacgaaacta acgtacgagt    420
catgcgctcc gaagaggcgt tctaagtgtt ttcgttgcgc caaacggttg catccctaac    480
tctggtttag ggtagccatt aactccgttt ctaaggcggt cggtaccatt taatgggaag    540
atggacccct cgatcgctaa cgcacctgtt tcgcgtacac gctcgcctgc aacccgtcag    600
gtctttctcc atcgccccg atagataatc attgctgtat cctccaggct ctatccatgg    660
gttaaagaaa tataacaatc cctaaggggc atgagaggaa agtccccgga ttcctgggaa    720
agaaggctgc aaatgatatg gatcgtacca gaattcccta ggtaaataga catacatcat    780
aatgcaacca cgactagtca aatatgaggc gacactggta gcaattcata tggtggccga    840
ttgaggcgcg aatacccccct gaataccgaa gtaccgggtg aatgttctac ccactcaagc    900
acaaggtggt ggacaggccc cacgactccg tctacactag caaccatccg ggttcaagtc    960
ggctactacg gaacgaggag cgtcatctac gtcgtgagaa g                       1001
```

<210> SEQ ID NO 3
<211> LENGTH: 7
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 3

```
agccgac                                                                7
```

<210> SEQ ID NO 4
<211> LENGTH: 16
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 4

```
agcaactatc tgaacg                                                     16
```

<210> SEQ ID NO 5
<211> LENGTH: 14
<212> TYPE: DNA
<213> ORGANISM: Artificial
<220> FEATURE:
<223> OTHER INFORMATION: SGP nucleic acid polymer derived from SEQ ID
    NO:2

<400> SEQUENCE: 5
agcgagggcc atca                                                    14

<210> SEQ ID NO 6
<211> LENGTH: 21
<212> TYPE: DNA
<213> ORGANISM: Artificial
<220> FEATURE:
<223> OTHER INFORMATION: SGP nucleic acid polymer derived from SEQ ID
    NO:2

<400> SEQUENCE: 6
agcctggcat atcgtcaggt c                                            21

<210> SEQ ID NO 7
<211> LENGTH: 21
<212> TYPE: DNA
<213> ORGANISM: Artificial
<220> FEATURE:
<223> OTHER INFORMATION: SGP nucleic acid polymer derived from SEQ ID
    NO:2

<400> SEQUENCE: 7
agcccaaagg gccttcggct g                                            21

<210> SEQ ID NO 8
<211> LENGTH: 21
<212> TYPE: DNA
<213> ORGANISM: Artificial
<220> FEATURE:
<223> OTHER INFORMATION: SGP nucleic acid polymer derived from SEQ ID
    NO:2

<400> SEQUENCE: 8
agcagtctgt ctttcctggg a                                            21

<210> SEQ ID NO 9
<211> LENGTH: 21
<212> TYPE: DNA
<213> ORGANISM: Artificial
<220> FEATURE:
<223> OTHER INFORMATION: SGP nucleic acid polymer derived from SEQ ID
    NO:2

<400> SEQUENCE: 9
agcaacgcgg tttgccaacg t                                            21

<210> SEQ ID NO 10
<211> LENGTH: 21
<212> TYPE: DNA
<213> ORGANISM: Artificial
<220> FEATURE:
<223> OTHER INFORMATION: SGP nucleic acid polymer derived from SEQ ID
    NO:2

<400> SEQUENCE: 10
agccatggta aattaccctt c                                            21

```
<210> SEQ ID NO 11
<211> LENGTH: 4
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 11 agct                                                                        4

<210> SEQ ID NO 12
<211> LENGTH: 17
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 12
agcgattgcg tggacaa                                                         17

<210> SEQ ID NO 13
<211> LENGTH: 12
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 13
agcgcatgtg cg                                                              12

<210> SEQ ID NO 14
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 14
agcggacgtt gggcagtcca g                                                    21

<210> SEQ ID NO 15
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 15 agcggggget atctattagt a                                                    21

<210> SEQ ID NO 16
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 16
agcatggtct taagggatcc a                                                    21

<210> SEQ ID NO 17
```

```
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 17
agccgatgat gccttgctcc t                                              21

<210> SEQ ID NO 18
<211> LENGTH: 10
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 18
agcactcttc                                                           10

<210> SEQ ID NO 19
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 19
aacccattgc gtgcacaccg a                                              21

<210> SEQ ID NO 20
<211> LENGTH: 5
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 20 cgcga                                                                 5

<210> SEQ ID NO 21
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 21
tcttgtatac aggggccgcg a                                              21

<210> SEQ ID NO 22
<211> LENGTH: 21
<212> TYPE: DNA
<213> ORGANISM: Artificial
<220> FEATURE:
<223> OTHER INFORMATION: SGP nucleic acid polymer derived from SEQ ID
```

```
      NO:1
<220> FEATURE:
<221> NAME/KEY: misc_feature
<223> OTHER INFORMATION: This sequence is in 3' to 5' direction.

<400> SEQUENCE: 22
ttcgggtttc ccggaagccg a                                               21

<210> SEQ ID NO 23
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 23
aaggaccctg cacttaaacg a                                               21

<210> SEQ ID NO 24
<211> LENGTH: 13
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 24
aactaacgta cga                                                        13

<210> SEQ ID NO 25
<211> LENGTH: 14
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 25
gtcatgcgct ccga                                                       14

<210> SEQ ID NO 26
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 26
atgggaagat ggacccctcg a                                               21

<210> SEQ ID NO 27
<211> LENGTH: 21
<212> TYPE: DNA
<213> ORGANISM: Artificial
<220> FEATURE:
```

<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 27
gtctttctcc atcgcccccg a                                         21

<210> SEQ ID NO 28
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 28
tacatcataa tgcaaccacg a                                         21

<210> SEQ ID NO 29
<211> LENGTH: 19
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 29
ctagtcaaat atgaggcga                                            19

<210> SEQ ID NO 30
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 30
agcaattcat atggtggccg a                                         21

<210> SEQ ID NO 31
<211> LENGTH: 11
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 31
ttgaggcgcg a                                                    11

<210> SEQ ID NO 32
<211> LENGTH: 18
<212> TYPE: DNA
<213> ORGANISM: Artificial

<220> FEATURE:
<223> OTHER INFORMATION: SGP nucleic acid polymer derived from SEQ ID
    NO:1
<220> FEATURE:
<221> NAME/KEY: misc_feature
<223> OTHER INFORMATION: This sequence is in 3' to 5' direction.

<400> SEQUENCE: 32 atacccctg aataccga                                                      18

<210> SEQ ID NO 33
<211> LENGTH: 21
<212> TYPE: DNA
<213> ORGANISM: Artificial
<220> FEATURE:
<223> OTHER INFORMATION: SGP nucleic acid polymer derived from SEQ ID
    NO:1
<220> FEATURE:
<221> NAME/KEY: misc_feature
<223> OTHER INFORMATION: This sequence is in 3' to 5' direction.

<400> SEQUENCE: 33
ggtggtggac aggccccacg a                                                 21

<210> SEQ ID NO 34
<211> LENGTH: 21
<212> TYPE: DNA
<213> ORGANISM: Artificial
<220> FEATURE:
<223> OTHER INFORMATION: SGP nucleic acid polymer derived from SEQ ID
    NO:1
<220> FEATURE:
<221> NAME/KEY: misc_feature
<223> OTHER INFORMATION: This sequence is in 3' to 5' direction.

<400> SEQUENCE: 34
aagtcggcta ctacggaacg a                                                 21

<210> SEQ ID NO 35
<211> LENGTH: 20
<212> TYPE: DNA
<213> ORGANISM: Artificial
<220> FEATURE:
<223> OTHER INFORMATION: SGP-SGP nucleic acid polymer derived from SEQ
    ID NO:2
<220> FEATURE:
<221> NAME/KEY: misc_feature
<223> OTHER INFORMATION: This sequence is in 3' to 5' direction.

<400> SEQUENCE: 35
tcgggtttcc cggaagccga                                                   20

<210> SEQ ID NO 36
<211> LENGTH: 4
<212> TYPE: DNA
<213> ORGANISM: Artificial
<220> FEATURE:
<223> OTHER INFORMATION: SGP-SGP nucleic acid polymer derived from SEQ
    ID NO:2
<220> FEATURE:
<221> NAME/KEY: misc_feature
<223> OTHER INFORMATION: This sequence is in 3' to 5' direction.

<400> SEQUENCE: 36 tcga                                                                    4

<210> SEQ ID NO 37
<211> LENGTH: 10
<212> TYPE: DNA

```
<213> ORGANISM: Artificial
<220> FEATURE:
<223> OTHER INFORMATION: SGP-SGP nucleic acid polymer derived from SEQ
      ID NO:2
<220> FEATURE:
<221> NAME/KEY: misc_feature
<223> OTHER INFORMATION: This sequence is in 3' to 5' direction.

<400> SEQUENCE: 37
tcgccccga                                                              10

<210> SEQ ID NO 38
<211> LENGTH: 18
<212> TYPE: DNA
<213> ORGANISM: Artificial
<220> FEATURE:
<223> OTHER INFORMATION: SGP-SGP nucleic acid polymer derived from SEQ
      ID NO:2
<220> FEATURE:
<221> NAME/KEY: misc_feature
<223> OTHER INFORMATION: This sequence is in 3' to 5' direction.

<400> SEQUENCE: 38
tcggctacta cggaacga                                                    18

<210> SEQ ID NO 39
<211> LENGTH: 20
<212> TYPE: DNA
<213> ORGANISM: Artificial
<220> FEATURE:
<223> OTHER INFORMATION: SGP-SGP nucleic acid polymer derived from SEQ
      ID NO:1

<400> SEQUENCE: 39
agcccaaagg gccttcggct                                                  20

<210> SEQ ID NO 40
<211> LENGTH: 4
<212> TYPE: DNA
<213> ORGANISM: Artificial
<220> FEATURE:
<223> OTHER INFORMATION: SGP-SGP nucleic acid polymer derived from SEQ
      ID NO:1

<400> SEQUENCE: 40 agct                                                                    4

<210> SEQ ID NO 41
<211> LENGTH: 10
<212> TYPE: DNA
<213> ORGANISM: Artificial
<220> FEATURE:
<223> OTHER INFORMATION: SGP-SGP nucleic acid polymer derived from SEQ
      ID NO:1

<400> SEQUENCE: 41
agcggggct                                                              10

<210> SEQ ID NO 42
<211> LENGTH: 18
<212> TYPE: DNA
<213> ORGANISM: Artificial
<220> FEATURE:
<223> OTHER INFORMATION: SGP-SGP nucleic acid polymer derived from SEQ
      ID NO:1

<400> SEQUENCE: 42
agccgatgat gccttgct                                                    18
```

```
<210> SEQ ID NO 43
<211> LENGTH: 10
<212> TYPE: DNA
<213> ORGANISM: Artificial
<220> FEATURE:
<223> OTHER INFORMATION: shortened SGP nucleic acid polymer derived from
      SEQ ID NO:2

<400> SEQUENCE: 43
agcccaaagg                                                              10

<210> SEQ ID NO 44
<211> LENGTH: 4
<212> TYPE: DNA
<213> ORGANISM: Artificial
<220> FEATURE:
<223> OTHER INFORMATION: SGP-SGP nucleic acid polymer derived from SEQ
      ID NO:2

<400> SEQUENCE: 44 agct                                                                    4

<210> SEQ ID NO 45
<211> LENGTH: 10
<212> TYPE: DNA
<213> ORGANISM: Artificial
<220> FEATURE:
<223> OTHER INFORMATION: SGP-SGP nucleic acid polymer derived from SEQ
      ID NO:2

<400> SEQUENCE: 45 agcggggggct                                                             10

<210> SEQ ID NO 46
<211> LENGTH: 10
<212> TYPE: DNA
<213> ORGANISM: Artificial
<220> FEATURE:
<223> OTHER INFORMATION: Shortened SGP nucleic acid polymer derived from
      SEQ ID NO:2

<400> SEQUENCE: 46
agccgatgat                                                              10

<210> SEQ ID NO 47
<211> LENGTH: 10
<212> TYPE: DNA
<213> ORGANISM: Artificial
<220> FEATURE:
<223> OTHER INFORMATION: Shortened SGP nucleic acid polymer derived from
      SEQ ID NO:1
<220> FEATURE:
<221> NAME/KEY: misc_feature
<223> OTHER INFORMATION: This sequence is in 3' to 5' direction.

<400> SEQUENCE: 47
cggaagccga                                                              10

<210> SEQ ID NO 48
<211> LENGTH: 4
<212> TYPE: DNA
<213> ORGANISM: Artificial
<220> FEATURE:
<223> OTHER INFORMATION: SGP-SGP nucleic acid polymer derived from SEQ
      ID NO:1
<220> FEATURE:
<221> NAME/KEY: misc_feature
```

```
<223> OTHER INFORMATION: This sequence is in 3' to 5' direction.

<400> SEQUENCE: 48 tcga                                                                    4

<210> SEQ ID NO 49
<211> LENGTH: 10
<212> TYPE: DNA
<213> ORGANISM: Artificial
<220> FEATURE:
<223> OTHER INFORMATION: SGP-SGP nucleic acid polymer derived from SEQ
      ID NO:1
<220> FEATURE:
<221> NAME/KEY: misc_feature
<223> OTHER INFORMATION: This sequence is in 3' to 5' direction.

<400> SEQUENCE: 49
tcgccccga                                                              10

<210> SEQ ID NO 50
<211> LENGTH: 10
<212> TYPE: DNA
<213> ORGANISM: Artificial
<220> FEATURE:
<223> OTHER INFORMATION: Shortened SGP nucleic acid polymer derived from
      SEQ ID NO:1
<220> FEATURE:
<221> NAME/KEY: misc_feature
<223> OTHER INFORMATION: This sequence is in 3' to 5' direction.

<400> SEQUENCE: 50
tacggaacga                                                             10

<210> SEQ ID NO 51
<211> LENGTH: 8
<212> TYPE: DNA
<213> ORGANISM: Artificial
<220> FEATURE:
<223> OTHER INFORMATION: SGP Primer DJB7

<400> SEQUENCE: 51 gcgaggat                                                                8

<210> SEQ ID NO 52
<211> LENGTH: 8
<212> TYPE: DNA
<213> ORGANISM: Artificial
<220> FEATURE:
<223> OTHER INFORMATION: SGP primer DJB8

<400> SEQUENCE: 52 ggcactgc                                                                8
```

METHODS FOR MONITORING GENOMIC DNA OF ORGANISMS

This application claims the benefit of U.S. Provisional Application Ser. No. 60/591,596, filed Jul. 28, 2004, incorporated herein by reference in its entirety.

BACKGROUND OF THE INVENTION

1. Field of the Invention

The invention is directed to improved methods for rapid detection and classification of organisms based on the genomic information of the organisms.

2. Related Background Art

In the biotechnological field, there is a need for rapid detection and/or classification of organisms, such as bacteria and viruses, in a variety of samples (e.g., environmental and medical). For example, rapid detection of bacteria, and subsequent classification of the species and/or strain, may be necessary to provide quality assurance for, e.g., a local water supply, a hospital, or a food processing plant; i.e., it may be necessary to screen various samples, including but not limited to samples of air, dust, water, blood, tissues, plants, foodstuffs, etc., for the presence of contaminating organisms, and to classify the contaminating organisms prior to consumption, exposure, and/or use by the public, or during use by the public. The present invention accomplishes these goals by improving methods for the detection and classification of organisms (e.g., bacteria or viruses) in a sample.

Standard microbiological methods for detecting and/or classifying an organism, e.g., culturing and Gram staining or testing of other biochemical properties, are imprecise and often cannot differentiate among different organisms, let alone different strains of an organism. More precise methods for detecting and/or classifying an organism are based on the genomic DNA of the organism. Such methods have advanced from tedious and conventional processes, such as northern blotting and RT-PCR, to cutting edge DNA microarray analysis. One such well-known method of detection and/or classification is the polymerase chain reaction (PCR).

PCR is effectuated by two separate and distinct (first and second) primers, each of which is respectively complementary to a nucleotide sequence found on either of the two templates (i.e., strands) of the double-stranded genomic DNA. Since the sequences of the two primers are based on the sequences of the two genomic DNA templates, the two primers bind to and bracket a singular and isolated locus of the double-stranded genomic DNA. PCR using such a pair of primers results in the exponential amplification of double-stranded genomic DNA that is identical to the singular and isolated locus of the genome bracketed by nucleotide sequences complementary to the two primers, i.e., a locus of DNA flanked by a first primer binding site on the 3'-end of one genomic DNA template and a second primer binding site on the 3'-end of the other genomic DNA template.

Since PCR exponentially amplifies DNA, it may be used to detect small amounts of genomic material. However, because PCR requires primers that are specifically complimentary to sequences of the genomic material, which are known and bracket the locus of interest, it is limited in that it can only be used for the detection and classification of known organisms. In other words, the investigator is required to know or guess the classification of the organism (i.e., the appropriate pair of primers to use) prior to any attempts at detecting the organism. Another limitation of PCR is the inability of the investigator to obtain sequence information about the amplified DNA, other than information about the sequences complimentary to the two primers used in the analysis.

To overcome some of the limitations of PCR, methods of waveform profiling were developed (see, e.g., the method of waveform profiling described in Japanese Patent Application Publication Nos. 2003-334082 and 2003-180351). Waveform-profiling methods provide ways to analyze and profile genomic material (e.g., DNA isolated from organisms such as bacteria) without requiring the investigator to know or guess the classification of the organism prior to detection. Briefly, waveform profiling generally analyzes the genomic DNA of the organism using multiple copies of a unique primer and the two denatured strands of the genomic DNA as templates to linearly amplify several distinct single-stranded nucleic acid polymers that form higher-order structures, e.g., triplexes, tetraplexes (or quadruplexes), etc. Because the genomic DNA of the organism is used as the template, the resulting single-stranded nucleic acid polymers will be distinct and contain sequences unique to the organism. Thus, the single-stranded nucleic acid polymers will form higher-order structures based on sequences unique to the organism. Accordingly, detection of such unique higher-order structures, which can be accomplished using detectable agents, e.g., fluorescent intercalators, may classify the organism.

The several distinct single-stranded nucleic acid polymers are usually produced using a single pattern generative waveform primer characterized by its structure and length. A waveform primer generally consists of two portions, a nonspecific stabilizing portion and a specific portion. As discussed below, the nonspecific stabilizing portion may help guide the formation of higher-order structures. In contrast, the specific portion guides the waveform primer to specifically bind to sequences complementary to its own sequence. The length of the waveform primer (e.g., 8-30 bases in length) is usually critical because it allows the specific portion of the primer to bind specifically to several discrete primer-binding sites, i.e., sequences complementary to the waveform primer, along the length of a genomic DNA template. The binding of waveform primers to several primer-binding sites along each single-stranded genomic DNA template allows for the generation of several distinct single-stranded nucleic acid polymers, the generation of which is critical to this method.

In addition to utilizing a waveform primer, these methods of waveform profiling also utilize several cycles of linear amplification to provide multiple copies of each of several distinct single-stranded nucleic acid polymers; therefore, many copies of the waveform primer are added to a solution containing the genomic DNA of interest prior to the first cycle of linear amplification. One cycle of linear amplification comprises the following steps: 1) denaturing, i.e., providing conditions that allow denaturation of double-stranded DNA into separate or individual single strands (e.g., each copy of the double-stranded genomic DNA denatured into two single-stranded genomic DNA templates); 2) annealing, i.e., providing conditions that allow the binding of complementary single-stranded DNA to each other (i.e., the waveform primer annealed to several discrete primer-binding sites on each single-stranded genomic DNA template); and 3) elongating, i.e., providing conditions that allow DNA polymerase-directed elongation of primer sequences over regions of template DNA, (e.g., several distinct single-stranded nucleic acid polymers elongated from each of several waveform primers bound to primer-binding sites along each genomic DNA template).

During one cycle of linear amplification, the temperature of the genomic DNA is increased (e.g., to 95-98° C.) to denature each copy of the genomic DNA into two single-stranded genomic DNA templates. The temperature is subsequently decreased (e.g., to 25° C.) to allow waveform primers to bind to several discrete primer-binding sites along the length of each denatured genomic DNA template. The final step in the cycle, elongation of several distinct single-stranded nucleic acid polymers from each bound waveform primer, is performed at ~72° C. using a polymerase, e.g., Taq polymerase. After this final step, the cycle repeats. During the next denaturing step, the several distinct nucleic acid polymers are denatured from the genomic DNA templates and become single-stranded nucleic acid polymers, wherein each single-stranded nucleic acid polymer has a 5'-to-3' nucleotide sequence comprising the nucleotide sequence of the waveform primer from which the single-stranded nucleic acid polymer was elongated, followed by a distinct nucleotide sequence that is complementary to the sequence of the region of the genomic DNA template that was downstream of the genomic DNA sequence that bound to a waveform primer. Since each single-stranded nucleic acid polymer comprises the sequence of the waveform primer at its 5'-end, each single-stranded nucleic acid polymer also comprises the nonspecific stabilizing portion of the waveform primer. The nonspecific stabilizing portion of the waveform primer generally guides each single-stranded nucleic acid polymer to form higher-order structures and prevents the recently elongated single-stranded nucleic acid polymers from binding to any waveform primer in subsequent cycles of amplification.

As a result of the nonspecific stabilizing portion of the waveform primer, the single-stranded nucleic acid polymers are not used as templates in subsequent cycles of amplification and each cycle of amplification is linear. In other words, each cycle of amplification produces only a single copy of each of the several distinct single-stranded nucleic acid polymers containing sequences unique to the organism, i.e., sequences complementary to sequences of the genomic DNA template that are downstream of waveform primers bound to primer-binding sites. Thus, in contrast to PCR, waveform-profiling methods generally do not result in exponential amplification of the several distinct single-stranded nucleic acid polymers containing sequences unique to the organism.

Each single-stranded nucleic acid polymer contains a base sequence complementary to a sequence of a genomic DNA template that is downstream of a waveform primer bound to a primer-binding site, so differences in base sequences present on multiple sites of different genomic DNAs may be compared and distinguished. As described above, the multiple copies of each of several distinct single-stranded nucleic acid polymers will interact with each other to form higher-order structures, i.e., complexes (e.g., triplexes and tetraplexes) comprising one or more single-stranded distinct nucleic acid polymers. The higher-order nucleic acid structures will have different stabilities and dissociate at different melting temperatures (Tm) depending on the base sequences of single-stranded nucleic acid polymers, i.e., based on the unique genomic information of the organism.

Waveform profiling generally requires that the melting temperature (Tm) of the various different higher-order structures, produced using the genomic DNA of a particular organism as a template, be determined and recorded; this can be accomplished with the use of fluorescent agents that intercalate into higher-order DNA structures, i.e., intercalators. The higher-order DNA structures generated by waveform profiling may be dissociated by increasing the temperature of the sample. As the higher-order DNA structures dissociate, the fluorescent agents intercalated in these higher-order structures will also dissociate. Melting temperature analysis plots the rate of change of fluorescence intensity obtained by the dissociation of these higher-order structures as a function of increasing temperature and produces a waveform that is unique to the genomic DNA of the organism and the utilized waveform primer, i.e. the dissociation of higher-order DNA structures at different Tm are observed and recorded to produce a characteristic "waveform profile" for each species (or strain) of organism, e.g., bacteria. Thus, waveform profiling may be used to obtain a unique waveform profile for each organism, and subsequent melting temperature analysis may be used to detect the unique waveform profile and to distinguish between genomic DNA isolated from a first organism and genomic DNA isolated from a second organism.

One of skill in the art will recognize that prior to performing a waveform-profiling method that produces a waveform profile, a sample containing an organism must be obtained and the genomic DNA must be extracted and isolated from the sample containing the organism. Methods of sample collection and genomic DNA extraction and isolation are well known in the art.

Since the above-described method (related to waveform profiling) relies on linear amplification, one of the difficulties of using this method is the requirement for a large starting amount of genomic DNA from the particular organism (e.g., bacteria) to be detected and/or classified. Consequently, waveform-profiling methods may be used to detect and classify organisms only if the organisms are present in large numbers (e.g., $10^6$ or more organisms) within a given sample, but are not effective for detecting and/or classifying a very small number of organisms.

Accordingly, waveform-profiling methods are generally not useful in detecting and/or classifying an organism present in small numbers, e.g., in a sample taken from a water supply or source at the onset of contamination. Although PCR may resolve the limitation of waveform-profiling methods that requires a large starting sample (because PCR results in the exponential amplification of the genomic DNA and allows for the detection of organisms present in small numbers), it is known in the art that waveform profiles produced using the complementary double-stranded pieces of DNA that result from PCR amplification are insufficient for classification of particular genomic sequences (see, e.g., "Goodbye DNA Chip, Hello Genopattern for $21^{st}$ Century," printed and distributed by Adgene Co., Ltd.). In other words, the prior art explicitly teaches it is not possible to compare, differentiate and classify genomic material (from various species or strains of organisms) using melting temperature (Tm) analysis of standard PCR products.

The present invention provides needed improvements to the above-described waveform-profiling methods to overcome the requirement that the organism be present in a large number in a sample for detection and classification. In particular, the present invention provides novel improvements that adapt and upgrade waveform-profiling methods such that a modified version of PCR may be incorporated. One of skill in the art will recognize that the present improvements to waveform-profiling methods will allow for the detection and classification of an organism even if the organism is present in a small number, e.g., the number of organisms present in a sample, even at the onset of contamination of a water supply or source.

SUMMARY OF THE INVENTION

It is one of the objects of the present invention to provide methods for detecting and classifying an organism that may be present in a small number, such that early safety and quality assurance regarding, e.g., a water supply, can more accurately be provided. As such, the invention provides improved methods, collectively referred to herein as Single Genome Profiling (SGP).

SGP requires the use of a primer (an "SGP primer") for the amplification of several distinct "SGP nucleic acid polymers." An SGP primer is characterized by its length and ability to bind specifically to several discrete sites along the length of the genomic DNA. Since an SGP primer does not comprise a nonspecific stabilizing portion, SGP nucleic acid polymers (elongated from the SGP primers of the invention bound to several discrete SGP primer-binding sites on, e.g., a single-stranded genomic DNA template) are free to bind SGP primers in subsequent amplification reactions. Because an SGP primer may bind specifically to complementary nucleotide sequences along the length of single-stranded SGP nucleic acid polymers, an SGP primer also functions as both a forward and reverse primer (in a modified version of PCR, i.e., "mPCR") to allow the amplification of several distinct "SGP-SGP nucleic acid polymers," each of which comprises a nucleotide sequence identical to the sequence of one of several regions of genomic DNA that are bracketed by SGP primer-binding sites, i.e., each SGP-SGP nucleic acid polymer sequence has at its 5'-end the sequence of the SGP primer and at its 3'-end the reverse complement of the SGP primer. Consequently, amplification of the several distinct SGP-SGP nucleic acid polymers comprising a nucleotide sequence of the SGP primer and the reverse complement sequence of the SGP primer occurs in an exponential (nonlinear) fashion, and enables using the present invention to detect and classify the genomic DNA of an organism, even if the organism is present in a small number. One of skill in the art will recognize that in practicing the present invention on RNA-based genomes (e.g., that of a retrovirus), a reverse transcription reaction should be performed prior to beginning SGP and the associated mPCR cycles.

The invention also provides a "half-time elongation step" associated with the final amplification cycle. In the present invention, the length of time for the elongation step associated with the final amplification cycle comprises a decrease in time (preferably the decrease in the length of time is approximately 40-60%; more preferably the decrease in the length of time is approximately 50%) resulting in a "half-time" elongation step in a final amplification cycle. Such a half-time elongation step typically will eliminate the exponential amplification of many SGP-SGP nucleic acid polymers because there will be insufficient time for elongation of the nucleic acid polymer from the SGP primer to the reverse complement of the SGP primer. Thus, shortened versions of SGP nucleic acid polymers ("shortened SGP nucleic acid polymers") will be produced from SGP-SGP nucleic acid polymers in the half-time step. One of skill in the art will recognize that, by performing the half-time elongation step subsequent to several cycles of exponential amplification with the modified version of PCR, i.e., mPCR, many copies of each of the shortened SGP nucleic acid polymers will be produced. Additionally, during a subsequent denaturing step, the shortened SGP nucleic acid polymers will become single-stranded. Ultimately, the shortened single-stranded SGP nucleic acid polymers form the higher-order structures that are detected in practicing the present invention with mPCR.

The present invention also provides the primers used in the improved methods, and methods for making these primers, as well as methods that utilize the exponential amplification and reduce the variability of waveform-profiling method. In one embodiment, an SGP primer of the invention has the nucleotide sequence set forth as SEQ ID NO:51. In another embodiment, an SGP primer of the invention has the nucleotide sequence set forth as SEQ ID NO:52.

In one embodiment, the invention provides an improved method of waveform profiling, the improvement comprising the use of an SGP primer. A skilled artisan will recognize that use of an SGP primer will effectuate mPCR. As such, the invention is directed toward a method of exponentially amplifying DNA, the method comprising mixing the DNA with a first mixture to form an amplification mixture, wherein the first mixture comprises multiple copies of an SGP primer and other amplification reagents at appropriate concentrations; denaturing the amplification mixture for a first length of time; annealing the amplification mixture for a second length of time; elongating the amplification mixture for a third length of time; and repeating the steps of denaturing, annealing, and elongating at least once. In some embodiments, the improvement further comprises the step of half-time elongation. In other embodiments, the SGP primer has a nucleotide sequence selected from the group consisting of the nucleotide sequence set forth as SEQ ID NO:51 and the nucleotide sequence set forth as SEQ ID NO:51. In another embodiment, the method further comprises, at any step, the step of adding a detectable agent.

An improved waveform-profiling method of the invention can be used to detect the absence or presence of, e.g., determine an organism in a sample. Thus, the invention provides a method of determining an organism in a sample, the method comprising the steps of acquiring the sample; subjecting the sample to extraction; introducing a first mixture to the sample to form an amplification mixture, wherein the first mixture comprises multiple copies of an SGP primer and other amplification reagents at appropriate concentrations; denaturing the amplification mixture at a first temperature for a first length of time; annealing the amplification mixture at a second temperature for a second length of time; elongating the amplification mixture at a third temperature for a third length of time; repeating the steps of denaturing, annealing, and elongating at least once; repeating the steps of denaturing and annealing; elongating the amplification mixture at a fourth temperature for a fourth length of time equal to about 40-60% of the third length of time (half-time elongation); allowing the formation of higher-order structures by cooling the amplification mixture; and detecting the absence or presence of higher-order structures, wherein the presence of higher-order structures determines the presence of an organism. In one embodiment of the invention, the fourth temperature is maintained for a fourth length of time about 50% of the third length of time. In another embodiment, the number of times the steps encompassing full-length elongation are repeated is 20-50 times, e.g., 20-25, 26-29, 30-40, 41-50 times. In one embodiment of the invention, the half-time elongation step(s) are repeated one or more times before allowing for formation of higher-order structures. In addition, the determining of the presence of an organism may determine the classification of the organism. In some embodiments, the third and fourth temperatures are the same temperature. Additionally, the invention provides methods of determining an organism in a sample further comprising at any step, the step of adding a detectable agent. The step of detecting in a method of the invention may comprise performing melting temperature analysis.

BRIEF DESCRIPTION OF THE DRAWINGS

FIG. 2: Nucleotide sequence of a theoretical genomic DNA.

FIG. 4: Sequences of each of the SGP nucleic acid polymers to be generated using the genomic DNA and primer of FIG. 3.

FIG. 5: Sequences of each of the SGP-SGP nucleic acid polymers to be generated after mPCR amplification of the SGP nucleic acid polymers of FIG. 4.

FIG. 6: Sequences of the SGP-SGP nucleic acid polymers (not underlined) and shortened SGP nucleic acid polymers (underlined) to be generated after the SGP-SGP nucleic acid polymers of FIG. 5 are subjected to a half-time elongation step.

DETAILED DESCRIPTION OF THE INVENTION

Figure 1B:
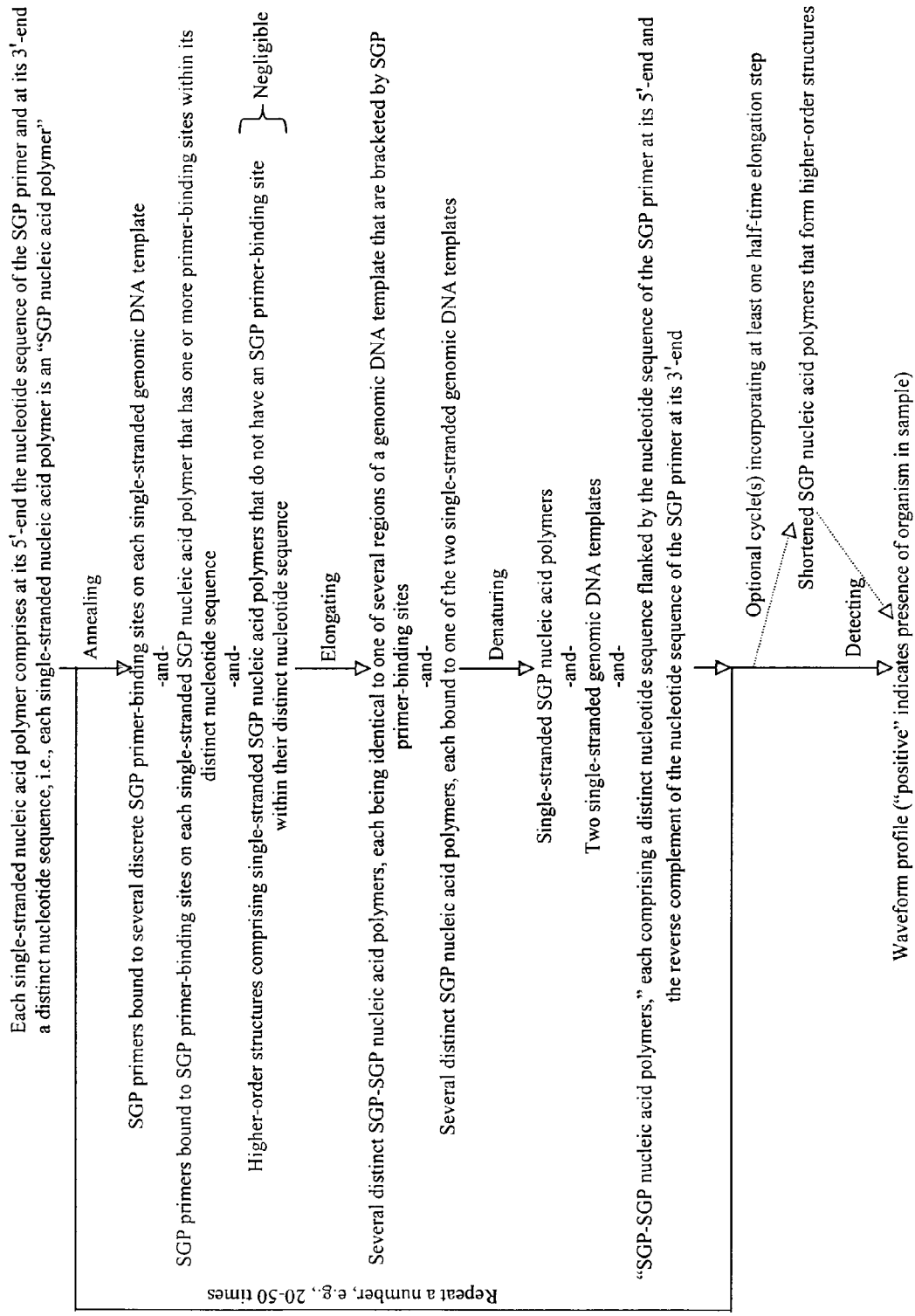
FIG. 1: Flow diagram delineating the steps of, and nucleic acid polymers resulting from, a waveform-profiling method and Single Genome Profiling method.

The present invention provides improvements to prior art methods of determining and/or classifying organisms. In the present invention it is not necessary to provide samples that contain a large number of organisms. In particular, the invention provides improvements to a method of waveform profiling. The improvements to the waveform-profiling method include improved primers that effectuate a modified version of PCR, i.e., exponential amplification of DNA. The improvements to the waveform-profiling method also include a half-time elongation step in the amplification procedure that allows for the production of a set of shortened single-stranded nucleic acid polymers derived from a subset of the nucleic acid polymers formed by the modified version of PCR (i.e., mPCR). The improvements to the waveform-profiling method allow for the detection and/or classification of an organism, even if the organism is present in a small number, e.g., the number of organisms present in a sample at the onset of contamination of a water supply. The present invention thus provides an improved waveform-profiling method that will aid in providing quality assurance related to many sources (e.g., environmental and medical) that may become contaminated with organisms, including, but not limited to, air, dust, water, blood, tissues, plants, and foodstuffs. One of skill in the art will recognize that the present invention relates to amplification of portions of a single genome, or a small number of genomes, as opposed to detection of a single genome; the detection follows amplification of portions of a single genome, or small number of genomes.

Single Genome Profiling (SGP) permits analyzing and profiling genomic DNA from an organism, even if the organism is present in a small number, by providing improvements to the waveform-profiling methods. These improvements include novel primers, ("SGP primers") and a modified version of polymerase chain reaction (mPCR). SGP additionally provides a final "half-time elongation step." These improvements permit SGP (i.e., methods using an SGP primer, mPCR, and a half-time elongation step) to result in the generation of distinct nucleic acid polymers ("SGP nucleic acid polymers"), each having a 5'-to-3' nucleotide sequence comprising the sequence of the SGP primer followed by a sequence complementary to one of several distinct regions of a genomic DNA template. In particular, SGP utilizes generated SGP nucleic acid polymers, the SGP primer, and mPCR to exponentially amplify "SGP-SGP nucleic acid polymers," each having a 5'-to-3' nucleotide sequence comprising the sequence of the SGP primer, a sequence identical to the sequence of one of several discrete regions of a genomic DNA template, followed by the reverse complement of the SGP primer. After exponential amplification of SGP-SGP nucleic acid polymers, SGP may introduce a novel half-time elongation step to generate shortened versions of SGP nucleic acid polymers, i.e., "shortened SGP nucleic acid polymers," that will form higher-order structures. Since the genomic DNA of the organism is used as the initial template, SGP nucleic acid polymers and SGP-SGP nucleic acid polymers will contain sequences unique to the organism. For the same reason, and because the resulting SGP-SGP nucleic acid polymers are used for the generation of shortened SGP nucleic acid polymers during the half-time elongation step, single-stranded shortened SGP nucleic acid polymers will contain sequences unique to the organism. As such, the single-stranded shortened SGP nucleic acid polymers form higher-order structures based on the sequences unique to the organism. Accordingly, the set of higher-order structures formed by the single-stranded shortened nucleic acid polymers are unique to the organism. Consequently, detection of the different higher-order structures that are formed enables detecting and/or classifying the organism; such detection can be accomplished using, for example, fluorescent intercalators.

A. Modified PCR (mPCR) of Single Genome Profiling

Many SGP nucleic acid polymers, and consequently, many SGP-SGP nucleic acid polymers and shortened SGP nucleic acid polymers may be generated using the modified PCR (mPCR) of the invention. Since each of these polymers originate from and contain an SGP primer at the 5'-end, many copies of the SGP primer must be added to a solution containing the genomic DNA of interest prior to the first cycles of mPCR in SGP. One of skill in the art will recognize that the materials (e.g., amplification reagents) and conditions of mPCR are similar to the well-known amplification reagents and conditions of PCR. For example, the appropriate concentrations of amplification reagents, e.g., polymerase, dNTPs reaction buffer, etc., to add to PCR in addition to the many copies of a primer pair and DNA template(s) are well known to a skilled artisan, as is the appropriate concentration of intercalators. The concentrations and amounts of amplification reagents, e.g., the SGP primer, nucleotides (i.e., dNTPs), DNA polymerase, reaction buffer, and/or magnesium that should be added prior to the first cycle of mPCR may be determined readily by a skilled artisan.

SGP is capable of analyzing the genomic DNA of organisms present in extraordinarily small amounts because it includes the step of MPCR. In one embodiment of the present invention, the genomic DNA of a single organism can provide the source template for a sufficient amount of shortened single-stranded nucleic acid polymers and associated higher-order structures for detection. This is because the mPCR step of SGP results in the exponential amplification of SGP-SGP nucleic acid polymers by virtue of the ability of the SGP primer to bind to and amplify certain SGP nucleic acid polymers in a manner somewhat similar to conventional PCR. However, there are two salient differences as compared with conventional PCR. First, the mPCR step utilizes only one primer, an SGP primer, which is capable of acting as both a forward and reverse primer. In contrast, conventional PCR uses two distinct primers: (1) a forward primer, and (2) a reverse primer that has a sequence different from that of the forward primer.

Second, whereas conventional PCR utilizes two primers to amplify a singular region of the genomic DNA, mPCR uses one primer to amplify several distinct regions of the genomic DNA, each of which are bracketed by a sequence identical to the SGP primer and a sequence complementary to the SGP primer, i.e., an "SGP primer-binding site." The ability of mPCR in SGP to amplify several distinct regions of the genomic DNA is due to the use of one SGP primer that is capable of acting as a forward and a reverse primer. This characteristic of the SGP primer is a function of its length, which allows two key events to occur: (1) binding of SGP primers to several discrete SGP primer-binding sites on each single-stranded genomic DNA template, and (2) binding of SGP primers to the SGP nucleic acid polymers (generated by at least one cycle of mPCR) that have a 5'-to-3' nucleotide sequence comprising the SGP primer sequence and the reverse complement of the SGP primer within its distinct nucleotide sequence. The presence of the reverse complement sequence within an SGP nucleic acid polymer and the subsequent binding of the SGP primer permits a PCR-like (i.e., mPCR) exponential amplification of several distinct double-stranded SGP-SGP nucleic acid polymers, i.e., the exponential amplification of several distinct regions of double-stranded genomic DNA that are bracketed by SGP primer-binding sites.

SGP primers, described in detail below, share some similar features with waveform primers, the latter described in detail in, e.g., Japanese Patent Application Publication Nos. 2003-334082 and 2003-180351. SGP primers are essential to SGP, and are characterized by their length. The length of an SGP primer is critical because the reduced length of the primer allows the primer to specifically bind to several discrete sites along the length of each single-stranded genomic DNA template, and because the reduced length also allows for the increased probability that SGP nucleic acid polymers will have a 5'-to-3' sequence comprising the reverse complement of the SGP primer sequence within its distinct nucleotide sequence.

The special characteristics of the SGP primer allow it to be used in the SGP method to result in the exponential, i.e., nonlinear, amplification of SGP-SGP nucleic acid polymers from certain SGP nucleic acid polymers during each cycle of MPCR after the first cycle. The first cycle of mPCR in SGP consists of the following steps: 1) denaturing each copy of the genomic DNA into two single-stranded genomic DNA templates, 2) annealing the SGP primer to several discrete SGP primer-binding sites on each single-stranded genomic DNA template, and 3) elongating SGP nucleic acid polymers from each of several SGP primers bound to discrete SGP primer-binding sites on each single-stranded genomic DNA template, wherein each SGP nucleic acid polymer has a 5'-to-3' nucleotide sequence comprising the bound SGP primer from which the SGP nucleic acid polymer is elongated, followed by a distinct nucleotide sequence that is complementary to the sequence of the genomic DNA template downstream of the bound SGP primer.

One of skill in the art will recognize that the "full-time" duration of the elongation step determines the length of the SGP nucleic acid polymers, and thus, SGP nucleic acid polymers created in one cycle may have distinct nucleotide sequences, but may be approximately the same length. For example, assuming the SGP primer is designed such that it will anneal to $10^3$ sites along each single-stranded genomic DNA template, and assuming that the timing of the elongation step is adjusted to produce SGP nucleic acid polymers of approximately 1 kb in length, one cycle of SGP amplification would result in $10^3$ distinct SGP nucleic acid polymers per template, each of which would be approximately 1 kb in length. Of course, if one of the SGP primer-binding sites to which the primer annealed is less than 1 kb from the 3'-end of a genomic DNA template, the elongation from the SGP primer bound at that site would produce an SGP nucleic acid polymer of less than 1 kb. In addition, if an SGP primer-binding site (e.g., site "B") is within 1 kb downstream of another SGP primer-binding site (e.g., site "A"), an SGP nucleic acid polymer of less than 1 kb will be generated from the SGP primer that bound at site A.

In SGP, a cycle of mPCR may be repeated more than once, e.g., 10-100 times. During the denaturing step of each cycle, SGP nucleic acid polymers will become single-stranded, i.e., the SGP nucleic acid polymers will no longer be bound to a genomic DNA template. It is critical in SGP, during the annealing step in subsequent cycles of mPCR, that certain SGP nucleic acid polymers having a 5'-to-3' nucleotide sequence comprising the reverse complement of the SGP primer within their distinct nucleotide sequence remain accessible to binding by the SGP primer, i.e., that these certain SGP nucleic acid polymers do not form higher-order structures. The binding of SGP nucleic acid polymers, either as part of a higher-order structure or to an SGP primer, is dependent on several factors, e.g., the annealing temperature, the lengths of the SGP nucleic acid polymers and SGP primers, and the concentrations of the SGP nucleic acid polymers and SGP primers in the reaction mixture. Consequently, manipulating the annealing step of mPCR, e.g., by increasing the concentration of the SGP primer, may aid in preventing the formation of higher-order structures comprising SGP nucleic acid polymers. However, while adjusting these well-known factors may aid in practicing the invention, such adjustments are not absolutely required because the factor of SGP nucleic acid polymer stability is addressed in the design of the SGP primer. As noted below, the SGP primer is designed without a nonspecific stabilizing portion, and thus, SGP nucleic acid polymers, each having the sequence of the SGP primer at its 5'-end, will not be stable, i.e., will tend to bind to primer readily. Consequently, certain SGP nucleic acid polymers that have a 5'-to-3' sequence comprising the SGP primer sequence followed by the reverse complement of the SGP primer sequence within their distinct nucleotide sequence will bind preferably to SGP primers prior to formation of any higher-order structure.

The binding of SGP primers to the certain SGP nucleic acid polymers that have a 5'-to-3' sequence comprising the SGP primer sequence followed by the reverse complement of the SGP primer sequence within their distinct nucleotide sequence effectuates SGP mPCR amplification cycles subsequent to the first cycle. An SGP primer binding to its complement on SGP nucleic acid polymers promotes a PCR-like reaction that results in SGP-SGP nucleic acid polymers, each of which has a nucleotide sequence comprising a sequence identical to the sequence of one of the several discrete regions of a genomic DNA template that are flanked at the 5'-end by a 5'-to-3' sequence identical to the SGP primer and at the 3'-end by a 5'-to-3' sequence that is the reverse complement of the SGP primer. Accordingly, since each SGP-SGP nucleic acid polymer has at its 3'-end a 5'-to-3' sequence that is complementary to the SGP primer, each SGP-SGP nucleic acid polymer will also be bound by the SGP primer prior to the formation of a higher-order structure in annealing steps of subsequent mPCR cycles. Consequently, subsequent cycles of mPCR will involve the exponential amplification of SGP-SGP nucleic acid polymers.

One of skill in the art will recognize that although all SGP nucleic acid polymers will comprise the SGP primer sequence at the 5'-end; only a certain percentage of the SGP nucleic acid polymers will also comprise the reverse complement of the SGP primer sequence within its 5'-to-3' distinct nucleotide sequence. The percentage of certain SGP nucleic acid polymers that participate in SGP-SGP nucleic acid amplification is dependent on several easily determined factors, such as the "full-time" length used for the "full-time elongation step" of mPCR, and the design of the SGP primer. For example, a potential SGP nucleic acid polymer may have the reverse complement of the SGP primer sequence approximately 750 bases (0.75 kb) downstream from the 5'-end. In this example, assuming, as above, that the full-time elongation step of mPCR is set to produce 1 kb SGP nucleic acid polymers, the subsequent mPCR cycles will begin an mPCR exponential amplification of that 750-base (0.75 kb) region, i.e., double-stranded SGP-SGP nucleic acid polymers that have the same sequence of a portion of the region of double-stranded genomic DNA from which the original 1 kb SGP nucleic acid polymer was derived. This exponential amplification will also occur at other locations in the genome for any other single-stranded SGP nucleic acid polymer that has a 5'-to-3' sequence containing the reverse complement of the SGP primer within 1 kb downstream of its 5'-end. Consequently, increasing the full-length elongation time will increase the probability that SGP nucleic acid polymers will comprise one or more SGP primer-binding sites within its nucleotide sequence. The converse is also true; decreasing the full-length elongation time will decrease the probability that SGP nucleic acid polymers will comprise one or more SGP primer-binding sites within its downstream sequence.

The percentage of SGP nucleic acid polymers that comprise SGP primer-binding sites within their sequence may also be manipulated by designing the primer, a fuller description of which is provided below, such that, e.g., 1 in 100 (i.e., $10^{-2}$) SGP nucleic acid polymers contain an SGP primer-binding site within the sequence. In such an example, and assuming as above that the SGP primer may anneal to $10^3$ sites along each single-stranded genomic DNA template, $2\times10^3$ different SGP nucleic acid polymers would be generated for each organism (i.e., $1\times10^3$ SGP nucleic acid polymers per template×2 templates per organism), and approximately 20 distinct SGP-SGP nucleic acid polymers would be amplified. Of course, the location of the reverse complement relative to the site at which the primer initially binds will determine the length of each SGP-SGP nucleic acid polymer being exponentially amplified. Additionally, as with any PCR-like procedure, exponential amplification of the SGP-SGP nucleic acids of the invention occurs through mPCR cycles that involve denaturing (resulting in single-stranded SGP-SGP nucleic acid polymers available for annealing to SGP primers), annealing of SGP primers (setting up the next cycle of elongating), and elongating (resulting in double-stranded SGP-SGP nucleic acid polymers to be amplified in the next cycle of amplification).

B. Half-Time Elongation Step

As noted above, the waveform analysis that serves as the final goal of a waveform-profiling method in SGP requires the presence of several distinct single-stranded nucleic acid polymers that represent the uniqueness of the genome; these nucleic acid polymers are combined with intercalators to form higher-order structures that may be subsequently detected.

In SGP, detectable higher-order structures are not formed until after 1) the exponential amplification of SGP-SGP nucleic acid polymers has been accomplished through several cycles of mPCR using full-time elongation steps, and 2) the generation of single-stranded shortened SGP nucleic acid polymers from SGP-SGP nucleic acid polymers through the introduction of a half-time elongation step. Prior to the generation of single-stranded shortened SGP nucleic acid polymers, the SGP-SGP nucleic acid polymers will be double-stranded and may be detected via conventional means, e.g., gel electrophoresis stained with ethidium bromide, melting temperature analysis, etc. However, for the generation of higher-order structures, the present invention allows for the introduction of a "half-time" cycle of amplification into the mPCR procedure (after sufficient mPCR cycles have produced sufficient copies of the exponentially amplified polymers; e.g., $10^6$ to $10^7$ copies) in order to produce several copies of each shortened SGP nucleic acid polymer. In other words, by decreasing the amount of time, e.g., by 40-60%, of the elongation step for this mPCR cycle, a subset of the nucleic acid polymers derived from the SGP-SGP nucleic acid polymers are decreased in length, i.e., shortened SGP nucleic acid polymers. Because the shortened SGP nucleic acid polymers will no longer contain the reverse complement of the primer sequence on the 3'-end of the polymer, shortened SGP nucleic acid polymers may not be exponentially amplified; i.e., they will remain single-stranded and will consequently form higher-order structures that may be detected.

It should be noted that SGP nucleic acid polymers (i.e., not shortened SGP nucleic acid polymers) not comprising a 5'-to-3' sequence identical to the reverse complement of the SGP primer would not be bound to primers during any cycle of mPCR amplification, and thus, may also form higher-order structures. However, as explained below, one half-time elongation step produces several copies of each distinct shortened SGP nucleic acid polymer (because they are derived from exponentially amplified SGP-SGP nucleic acid polymers). In contrast, SGP nucleic acid polymers not having a sequence comprising an SGP primer-binding site are only linearly amplified from a relatively small starting amount of genomic DNA. Consequently, the contribution of such SGP nucleic acid polymers to the formation of higher-order structures is negligible compared to the contribution of the shortened SGP nucleic acid polymers to the higher-order structures.

The higher-order structures produced in SGP will contain mostly shortened SGP nucleic acid polymers that are generated by introduction of the half-time elongation step. By way of example, assuming, as above, that the SGP primer could anneal to, e.g., approximately $10^3$ sites on each single-stranded genomic DNA template, the total number of SGP nucleic acid polymers from the first cycle may be, for example, approximately $2\times10^3$ SGP nucleic acid polymers per copy of genomic DNA (i.e., per organism). Also assuming, again as above, that the primer was designed such that 1 in 100 SGP nucleic acid polymers has a sequence comprising an SGP primer-binding site within its sequence, approximately 20 SGP-SGP nucleic acid polymers, each of which is identical to one of several distinct regions of a genomic DNA template that are bracketed by SGP primer-binding sites, will be exponentially amplified by MPCR, resulting in a relatively large number of copies of SGP-SGP nucleic acid polymers (approximately $10^6$-$10^7$ copies after 22-24 mPCR cycles when starting with a single genomic DNA). The number of exponentially amplified SGP-SGP nucleic acid polymers, and consequently the number of shortened SGP nucleic acid polymers derived therefrom, will dwarf the number of SGP nucleic acid polymers that continue to be produced by linear amplification as the cycles of amplification proceed.

One of skill in the art will recognize that the potential total number of SGP-SGP nucleic acid polymers produced by SGP is related to the size of the genome and the primer length. Thus the preferred number of SGP nucleic acid polymers produced in the first cycle of amplification may be determined as a function of the desired number of SGP-SGP nucleic acid polymers capable of producing shortened SGP nucleic acid polymers during the half-time elongation step (i.e., the desired number of shortened SGP nucleic acid polymers available for formation of higher-order structures). Such determination will be helpful in designing SGP primers of the invention, described in further detail below.

In determining the desired number of shortened SGP nucleic acid polymers available for the formation of higher-order structures, one of skill in the art will recognize that only a subset of the SGP-SGP nucleic acid polymers exponentially amplified by mPCR is used in the generation of shortened SGP nucleic acid polymers; such subset comprises the longer SGP-SGP nucleic acid polymers that are not able to fully elongate in a half-time elongation step. Since the sequences of SGP-SGP nucleic acid polymers being exponentially amplified by mPCR comprise the nucleotide sequence of the reverse complement of the primer at the 3'-end, a full-time elongation step is necessary to complete the elongation for this subset of SGP-SGP nucleic acid polymers, and the half-time elongation step will result in shortened SGP nucleic acid polymers, i.e., nucleic acid polymers that do not contain the reverse complement of the primer at the 3'-end. On the other hand, some of the SGP-SGP nucleic acid polymers being exponentially amplified by mPCR are considerably shorter than these longer SGP-SGP nucleic acid polymers. Such SGP-SGP nucleic acid polymers, which fully elongate in the time allotted in the half-time elongation step, will continue to be amplified exponentially in any subsequent cycles of mPCR; as described below, these SGP-SGP nucleic acid polymers commonly will not become part of the higher-order structures. Given the random location of the reverse complement of the SGP primer within the length of the SGP-SGP nucleic acid polymers that undergo exponential amplification with mPCR, the introduction of a half-time elongation step will result in approximately half of the SGP-SGP nucleic acid polymers being used to create shortened SGP nucleic acid polymers.

Approximately 50% of the exponentially amplified SGP-SGP nucleic acid polymers will not contain an SGP primer-binding site within the portion elongated by the half-time elongation step, and thus will participate in the generation of shortened SGP nucleic acid polymers. Since the shortened SGP nucleic acid polymers will not comprise a sequence capable of binding to the SGP primer for further mPCR cycles, they will form higher-order structures. The other approximately 50% of the SGP-SGP nucleic acid polymers exponentially amplified by mPCR will still contain an SGP primer-binding site. Additionally, since the annealing of SGP-SGP polymers with complementary sequences to create double-stranded SGP-SGP polymers is stable and tends to occur quickly, SGP-SGP nucleic acid polymers commonly will not be utilized in the formation of higher-order structures.

For example, assuming that an SGP primer of 9 bases in length may anneal to 7,000 sites, and the resulting SGP nucleic acid polymers may be elongated to 2,000 bases in length, $1.4 \times 10^7$ bases of genomic DNA, i.e., $1/142$ of a single-stranded genomic DNA template of, e.g., $2 \times 10^9$ bases in length, will be copied as SGP nucleic acid polymers. In SGP, approximately 50 to 70 of these 7,000 SGP nucleic acid polymers will comprise an SGP primer-binding site (assuming, as above, that the SGP primer was designed such that approximately 1 in 100 SGP nucleic acid polymers contain an SGP primer-binding site). These approximately 50 to 70 SGP nucleic acid polymers will effectively generate SGP-SGP nucleic acid polymers that will be exponentially amplified during the mPCR step(s) of SGP. After 22-24 cycles of mPCR and after the half-time elongation step, several copies (e.g., $10^6$-$10^7$) of approximately 25-35 distinct shortened SGP nucleic acid polymers (which will form the higher-order structures) are expected to result from the exponentially amplified SGP-SGP nucleic acid polymers. Thus, the half-time elongation step not only produces shortened SGP nucleic acid polymers for the formation of higher-order structure, but also distinguishes among SGP-SGP nucleic acid polymers of different lengths.

As a further example, assume that among the several SGP-SGP polymers being amplified exponentially during the full-time mPCR cycles in SGP are SGP-SGP nucleic acid polymers of 1 kb, 0.8 kb, 0.6 kb, 0.4 kb, and 0.2 kb; also assume that the timing of the elongation step in these repetitive mPCR cycles is just sufficient for elongating a 1 kb polymer. During the subsequent "half-time" elongation step, the resulting polymers produced will be approximately 0.5 kb, 0.5 kb, 0.5 kb, 0.4 kb and 0.2 kb, respectively. As this MPCR cycle progresses, and the newly elongated polymers of DNA are denatured from their individual complementary template strands, the first three listed polymers (i.e., the polymers of 0.5 kb in length, those copied from individual template strands that were originally of greater lengths (1 kb, 0.8 kb, and 0.6 kb)) will not have the reverse complement of the primer sequence at their 3'-end, and they will all be of approximately the same length (i.e., 0.5 kb). These single-stranded shortened SGP nucleic acid polymers will be available to form the higher-order structures necessary for the generation of waveform profiles. However, the polymers elongated from individual template strands of 0.4 kb and 0.2 kb lengths will be full length, i.e., the reverse complement of the primer sequence will be present at the 3'-end of these copies, and subsequent cycles of PCR amplification will continue to produce SGP-SGP nucleic acid polymers such that they will not be available to participate in the formation of higher-order structures.

C. Detecting the Single Genome Profile

Because exponential amplification, i.e., mPCR, is used in the SGP method, there is no requirement to begin with a large number of copies of the genomic DNA of interest. For example, assume that a (non-SGP) waveform primer may bind to $10^3$ sites along each single-stranded genomic DNA template and (because other waveform-profiling methods generally require beginning the procedure with at least $10^6$ organisms, as described above) the total number of nucleic acid polymers produced per cycle of linear amplification is approximately $2 \times 10^9$ ($10^3$ nucleic acid polymers per genomic DNA template $\times$ 2 genomic DNA templates per organism $\times 10^6$ organisms). In other waveform-profiling methods, the linear amplification cycles would be repeated, e.g., 22-24 times (i.e., producing 22-24 sets of $2 \times 10^3$ different single strands). In contrast, one of the embodiments of the present invention is related to the fact that waveform profiling with the SGP method potentially can be accomplished if only a single copy of the genomic sequence is present in the sample at the beginning of the amplification process (assuming efficient extraction). After several cycles of mPCR amplification (e.g., 22-24 cycles), beginning with one copy of the genome, each distinct region of genomic DNA bracketed by SGP primer-binding sites, i.e., each distinct SGP-SGP nucleic acid, will be copied on the order of $10^6$ to $10^7$ times (i.e., approximately $10^6$-$10^7$ copies will be present). This improvement over other waveform-profiling methods allows for far greater sensitivity in detecting and classifying, for example, the presence of bacteria in a sample using the SGP method.

Because the shortened SGP nucleic acid polymers are derived from SGP-SGP nucleic acid polymers that are identical to regions of the genomic DNA bracketed by SGP primer-binding sites, the shortened SGP nucleic acid polymers will comprise the unique sequence differences of the organism being detected. In SGP, the copies of each of the several single-stranded shortened SGP nucleic acid polymers produced during the half-time elongation step will interact with each other to form higher-order structures, i.e., complexes comprising a number of shortened SGP nucleic acid polymers. The higher-order structures will have different stabilities and dissociate at different melting temperatures (Tm) depending on the base sequences of the shortened single-strands, i.e., based on the unique genomic information of the organism. The Tm of the higher-order structures derived from an organism can be determined and recorded; this is accomplished with the use of fluorescent agents that intercalate into higher-order DNA structures, i.e., intercalators. Thus, SGP may be used to detect, compare and distinguish the genomic DNAs of different organisms through waveform profile analysis, i.e., detecting and recording the dissociation of higher-order structures.

The higher-order structures of a particular sample are dissociated by increasing the temperature of the sample. As the higher-order DNA structures dissociate, the fluorescent agents intercalated in these higher-order structures also dissociate. Plotting the rate of change of fluorescence intensity obtained by the dissociation of these higher-order structures as a function of increasing temperature produces a waveform that is unique to the genomic DNA of the organism, i.e. higher-order DNA structures at different melting temperatures (Tm) are observed and recorded to produce a characteristic waveform profile. A waveform profile that indicates the presence of an organism in the sample is termed a positive waveform profile; in the event that no organism is present in the sample, a negative waveform profile is produced.

In some embodiments of the present invention, the presence of an appropriate (positive) waveform profile is indicative of the presence of an organism in a sample. In other embodiments, a characteristic waveform profile is indicative of a particular species (or strain) of an organism, e.g., a species or strain of bacteria. Thus, the SGP method can distinguish between the genomic DNA from a first organism and the genomic DNA from a second organism using intercalators to obtain a unique waveform profile for each organism using a method of waveform profiling.

As described above, the mPCR step of SGP comprises multiple cycles of amplification; i.e., multiple cycles of the following steps: 1) denaturing each genomic DNA into genomic DNA templates, 2) annealing SGP primers to several discrete SGP primer-binding sites along each genomic DNA template and any previously generated SGP nucleic acid polymers and SGP-SGP nucleic acid polymers, and 3) elongating SGP and SGP-SGP nucleic acid polymers from each primer that annealed to an SGP primer-binding site. In particular, during one cycle of amplification, the temperature of the sample is increased (e.g., to 95-98° C.) to denature any double-stranded nucleic acid polymers (including genomic DNA). The temperature is subsequently decreased (e.g., to 25° C.) to allow SGP primers to anneal to any available SGP primer-binding site. The final step in the cycle, elongation of SGP and SGP-SGP nucleic acid polymers from the primer, is performed at ~72° C. using, e.g., Taq polymerase. Finally, in one of the last cycles of amplification, the length of time for the elongation step is reduced, e.g., by 40-60% (e.g., by 50%), to generate shortened SGP nucleic acid polymers. Additional cycles incorporating additional half-time elongation steps may be included in the present invention to produce a more accurate and/or robust waveform profile; these cycles may follow additional cycles incorporating additional full-time elongation steps included to amplify the products (e.g., SGP-SGP nucleic acid polymers of the invention).

One of skill in the art would know to employ an apparatus or machine capable of the repetitive cycling steps involving the alterations in temperature necessary for the denaturing, annealing, and elongating steps inherent in amplification procedures; such machines include, but are not limited to, PCR machines known in the art, and the "Genopattern Analyzer GP1000" machine (Adgene). Other companies that produce devices capable of the mPCR cycling steps necessary in the present invention include, but are not limited to, Perkin-Elmer (Wellesley, Mass.), Applied Biosystems (Foster City, Calif.), or MJ Research (Waltham, Mass.). Such machines are capable of altering the timing and duration of various steps in which temperatures are changed and reset, and thus such machines would be useful in producing both the full-time elongation steps and the essential half-time elongation step of the present invention. In addition, one of skill might employ additional materials to assist in the various aspects of using SGP to detect the genomic DNA of organisms, including but not limited to reagent kits for extraction (of which there are several known in the art; e.g., Xtrana technologies, such as the Xtra Amp® extraction system (Xtrana Inc., Broomfield, Colo.)); analytical software to interpret the results produced by waveform profiling (e.g., GenoMaster by Adgene); and primer-design supporting tools (such as the "Design Support Tool for Genopattern Primer" used in other waveform-profiling methods, and GenoSequenceAnalyzer software, both by Adgene). One of skill in the art would adjust the parameters and/or protocols of such software and/or tools to be useful for SGP.

D. Single Genome Profiling Primers

An SGP primer is designed, using methods well known in the art, such that it binds to several discrete sites along each single-stranded genomic DNA template. In one embodiment of the invention, SGP primers are used to detect the presence of any genomic DNA from an organism, e.g., bacteria and viruses. In another embodiment of the invention, SGP primers are tailored for use in detecting particular organisms, e.g., a particular species or strain of bacteria. One of skill in the art can determine the length and sequence of an SGP primer that is used to detect the genomic DNA of bacteria generally, or of a particular species or strain of bacteria, by taking into account the length and sequence of the genomic DNA. One of skill in the art would survey several species of bacteria regarding the sequences of their genomic DNAs and deduce the sequence of a primer capable of detecting most or all of these species; this type of primer is sometimes referred to as a "universal" primer. Universal SGP primers, and SGP primers specific for a particular species or strain, are determined after straightforward experimental trials conducted by one of ordinary skill in the art.

One of skill in the art will appreciate that the length of the SGP primer and its ability to bind to several SGP primer-binding sites, i.e., complementary sequences, along genomic DNA templates are inversely related, i.e., the shorter the primer, the greater the number of discrete SGP binding sites along a genomic DNA template to which the primer will bind. Conversely, the longer the primer, the fewer the number of discrete SGP primer-binding sites along a genomic DNA template to which the primer will bind. In addition, the same analysis related to primer length applies to the probability that the complementary sequence of the SGP primer and the reverse complementary sequence of the SGP primer will occur within a preset distance along the length of a genomic DNA template (i.e., the preset maximum length of an SGP nucleic acid polymer). Thus, the shorter the primer, the greater the likelihood that the reverse complement of the SGP primer-binding site will be present within a preset distance downstream from the SGP primer-binding site. The preset distance is determined by the length of time comprising the full-time elongation step, and when the reverse complement of the primer-binding site is present within that preset distance, exponential amplification will occur. In addition to the short length of an SGP primer, parameters affected by and/or related to the sequence content of the primer, e.g., the melting temperature of the primer, the G/C content of the primer, a GC clamp, self-complementarity of the primer, etc., play a role in the design of the primer. Designing primers with these parameters in mind has become a routine method in the art (see generally, e.g., Burpo (2001) "A critical review of PCR primer design algorithms and cross-hybridization case study," available in "Computational Molecular Biology" course materials, Stanford University (cmgm.stanford.edu/biochem218/Projects %202001/Burpo.pdf)).

Consequently, a skilled artisan will be able to design an appropriate SGP primer by taking into account the length and sequence of the genomic DNA, and the desired length and specificity of the primer. In one embodiment of the invention, the SGP primer is designed so that it binds with each single-stranded genomic DNA template with a predetermined frequency. In another embodiment of the invention, the SGP primer is designed such that the primer also can act as a forward and reverse primer in the exponential amplification of SGP nucleic acid polymers with a predetermined frequency.

One of skill in the art would also look to the materials and software programs related to other waveform-profiling methods and the generation of waveform primers (available from, e.g., Adgene) as an aid in designing primers for SGP (including "universal" primers, and primers for detection of particular species and strains of, e.g., bacteria). However, one of skill would recognize the need to refine the techniques and parameters related to other waveform-profiling methods for designing primers in order to produce primers that function correctly in SGP. For example, other waveform-profiling methods utilize primers that contain both a specific portion and a nonspecific, stabilizing portion; the SGP primers of the present invention do not contain a nonspecific stabilizing portion. In addition, one of skill will recognize that it is necessary for the SGP primers to bind to a greater number of binding sites along each single-stranded genomic DNA template (as compared to primers in other waveform-profiling methods), at least in part because only a percentage of the SGP nucleic acid polymers will have a sequence comprising the reverse complement of the primer within the preset distance downstream from the primer-binding site, i.e., only a percentage will undergo exponential amplification and result in SGP-SGP nucleic acid polymers. Further, only a percentage (e.g., approximately 50%) of SGP-SGP nucleic acid polymers that undergo exponential amplification will produce shortened SGP nucleic acid polymers during a half-time elongation step.

Primers for SGP are designed to be shorter (less bases) than primers used in other waveform-profiling methods (or those used in standard PCR) because the probability that SGP-SGP nucleic acid polymers are produced is increased as the primer length is decreased. For this reason, one of skill in the art would design primers of shorter length than those suggested/recommended for other waveform-profiling methods. For example, Adgene presents an example of a waveform primer in FIG. 4 of "A Method for Comparison and Identification of DNAs and RNAs by Pattern Analysis: Genopattern Method" (available from Adgene). This waveform primer contains an eleven-base nonspecific stabilizing portion and an eight-base specific portion. One of skill would design primers for SGP by excluding the nonspecific portion, and might also reduce the number of bases in the total SGP primer to a number less than the number of bases in the specific portion of Adgene's waveform primer. For example, a primer of six or seven bases in length could be designed for use in SGP. In other embodiments in which the specific portion of a particular waveform primer contains more bases, the design for a corresponding SGP primer may, in turn, contain more bases as well.

Among the bacteria that can be detected by the SGP method are those for which universal waveform primers have already been designed; such primers are known in the art and are useful in detecting *Vibrio parahaemolyticus; Pseudomonas aeruginosa; Salmonella typhimurium; Klebsiella pneumoniae; Campylobacter jejuni; Shigella sonnei; Enterococcus faecalis; Haemophilus influenzae; Helicobacter pylori; Streptococcus pyogenes; Mycobacterium bovis; Escherichia coli; Bacillus cereus; Staphylococcus aureus*; and *Bacillus subtilis*. Other primers, several of which can be used to distinguish among individual species and strains of bacteria, are also available from Adgene for use in other waveform-profiling methods. As noted above, one of skill would alter the design of the primer, or change the method of designing the primer, in order to produce a primer useful in SGP based on the known waveform primer. In addition, one of skill in the art would design appropriate SGP primers for organisms for which no waveform primer has been designed (for example, for other bacteria and viruses) by analysis of the genomic material of the organism(s) of interest, and by conducting a series of straightforward experimental trials.

One of skill in the art will recognize the applicability of SGP in testing a sample, e.g., a water sample. Methods for isolating organisms, and consequently the genome of the organism, will depend on the sample and are well known in the art. Once potential genomic DNA is isolated, the SGP method may be used to detect the presence of genomic DNA, and thus, the presence of an organism. In certain situations, e.g., when the sample should be sterile or relatively free of contamination, e.g., a water sample, such detection is sufficient to detect contamination by an organism. Where classification of the organism is required, other and more specific SGP primers may be used.

EXAMPLES

Embodiments of the invention are discussed herein. The basis of one embodiment of the invention, i.e., the basis of a system for detecting the absence or presence of a contaminating organism in a sample, is found in Example 1. Application of the invention is found in Example 2. One of skill in the art will recognize the utility of such a system in providing quality assurance for various samples, e.g., for detecting the absence or presence of bacteria in a water supply. Again, it will be recognized by one of skill in the art that the present invention may be used to analyze the absence or presence of genes and other lengths of nucleotides in different samples. For example, one of skill in the art could use the present invention to detect and classify anthrax in a sample filtered from an air supply or in a sample of blood, or detect and classify a virus coated on various foodstuffs. The present invention should not be construed to be limited to the scope of the specific examples described below.

Example 1

Figure 1C:
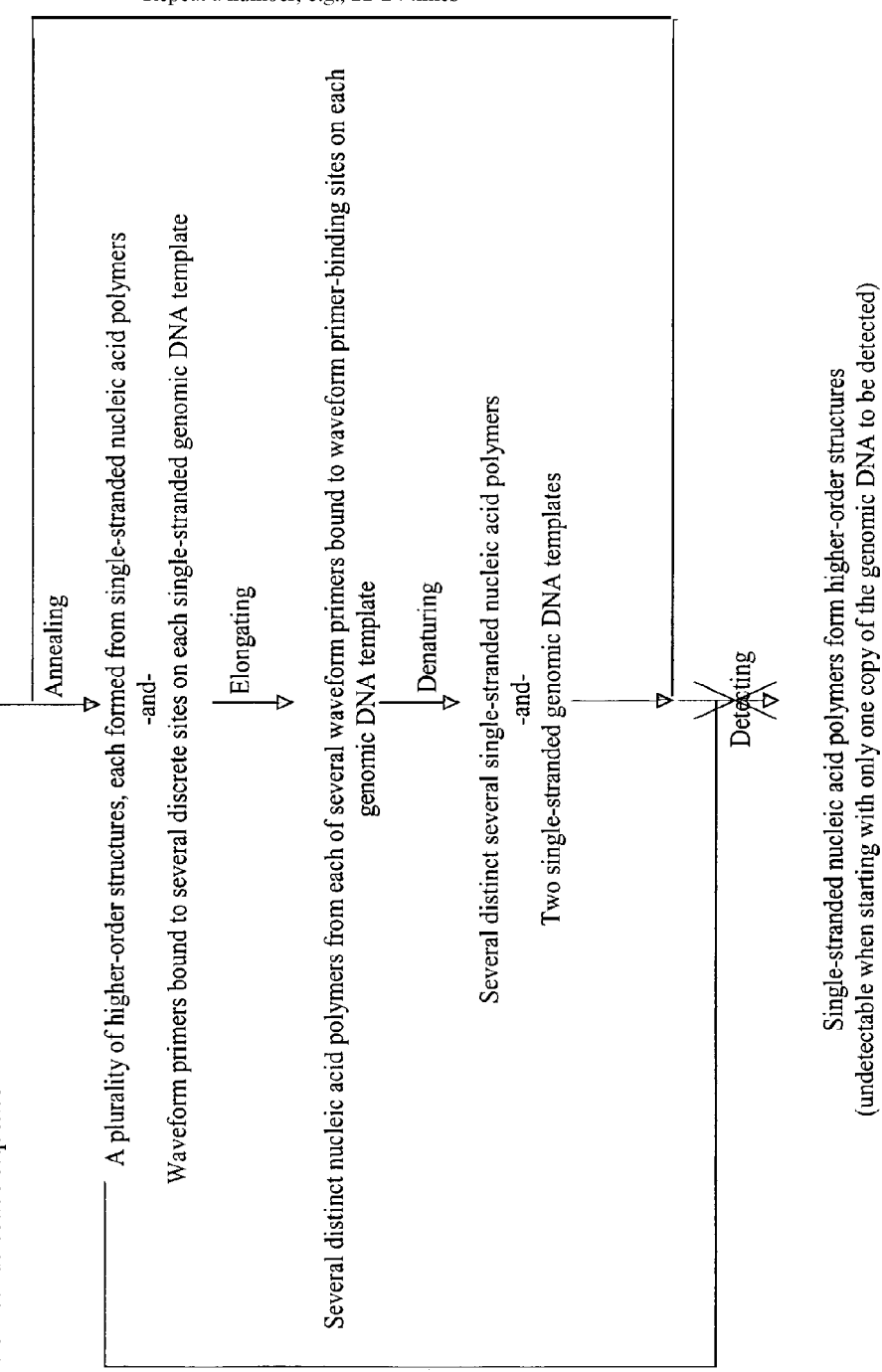

The Single Genome Profile (SGP) Method Comprising Modified PCR (mPCR) and Half-Time Elongation Step The examples and figures provided below are theoretical constructions provided to aid one of skill in the art in an understanding of the invention, as well as to delineate the improvements described herein. FIG. 1 is a flow diagram that delineates the first cycle of waveform-profiling methods, including the SGP method (FIG. 1A) and compares the results of subsequent cycles of the SGP method (FIG. 1B) and other waveform-profiling methods (FIG. 1C). It should be noted that the flow diagram represents the use of one copy of the genomic DNA to be detected. However, as discussed above, only with the SGP method will this amount of genomic DNA be sufficient for the formation of detectable higher-order structures.

To further demonstrate the invention, both a theoretical primer sequence and a theoretical genomic sequence are provided in Example 1.1 and Example 1.2, respectively, to demonstrate how a primer of sufficiently short length will be able to bind to several discrete primer-binding sites along the length of each single-stranded genomic DNA template. Example 1.3 then guides one of skill in the art through the SGP process described herein, provides the sequences of each nucleic acid polymer expected after each step of the SGP method, and helps to delineate the improvements of the invention. The examples presented herein should not be construed or understood as limiting the scope of the invention.

Example 1.1

Theoretical Primer Sequence

In the model provided herein, the primer is 5'-AGC-3'.

Example 1.2

Theoretical Genomic sequence

A 1001 bp genomic sequence (of which the two stands are set forth as SEQ ID NO:1 and SEQ ID NO:2, respectively) containing the four DNA nucleotide bases (adenine "A," guanine "G," thymine "T," and cytosine "C") in random order and frequency was generated by use of a computer program. A few bases of this theoretical, randomly generated sequence were altered in order to obtain a sequence that more clearly demonstrates the SGP method. The sequence of each of the single-stranded genomic DNA templates of the double-stranded genomic DNA is shown in FIG. 2. The sequence of one of the single-stranded genomic DNA templates is presented 5'-to-3', represented by uppercase letters corresponding to the nucleotide bases, and set forth as SEQ ID NO:1; the complementary single-stranded genomic DNA template is presented 3'-to-5', represented by lowercase letters corresponding to the nucleotide bases, and set forth as SEQ ID NO:2. Bolded letters on each genomic DNA template show the sites at which the theoretical primer of Example 1.1 is expected to anneal, i.e., primer-binding sites. The bracketed regions in FIG. 2 demonstrate the several discrete regions of the theoretical genomic DNA that are bracketed by primer-binding sites, each of which will be exponentially amplified in the form of SGP-SGP nucleic acid polymers (see, e.g., FIG. 5).

Example 1.3

SGP Method Comprising Modified PCR and a Half-Time Elongation Step

The primer of Example 1.1 is expected to anneal to each primer-binding site along the genomic DNA of Example 1.2. The first cycle of mPCR begins with denaturing the genomic DNA into two genomic DNA templates, which is performed at ~95-98° C. for approximately 2 minutes. Denaturing is followed by annealing of the primer to several discrete complementary sites, i.e., primer-binding sites, on each single-stranded genomic DNA template. Annealing occurs at ~25° C. for approximately 2 minutes. After the primer has annealed to several discrete complementary sites on each single-stranded genomic DNA template, a polymerase, e.g., Taq polymerase, elongates distinct nucleic acid polymers, i.e., SGP nucleic acid polymers, starting at the 3'-end of the primer and extending in 5'-to-3' direction. Elongation occurs at ~72° C. for approximately 2 minutes, and as such, in this theoretical first cycle of MPCR, SGP nucleic acid polymers of 21 bases or less are produced.

Figure 3A:
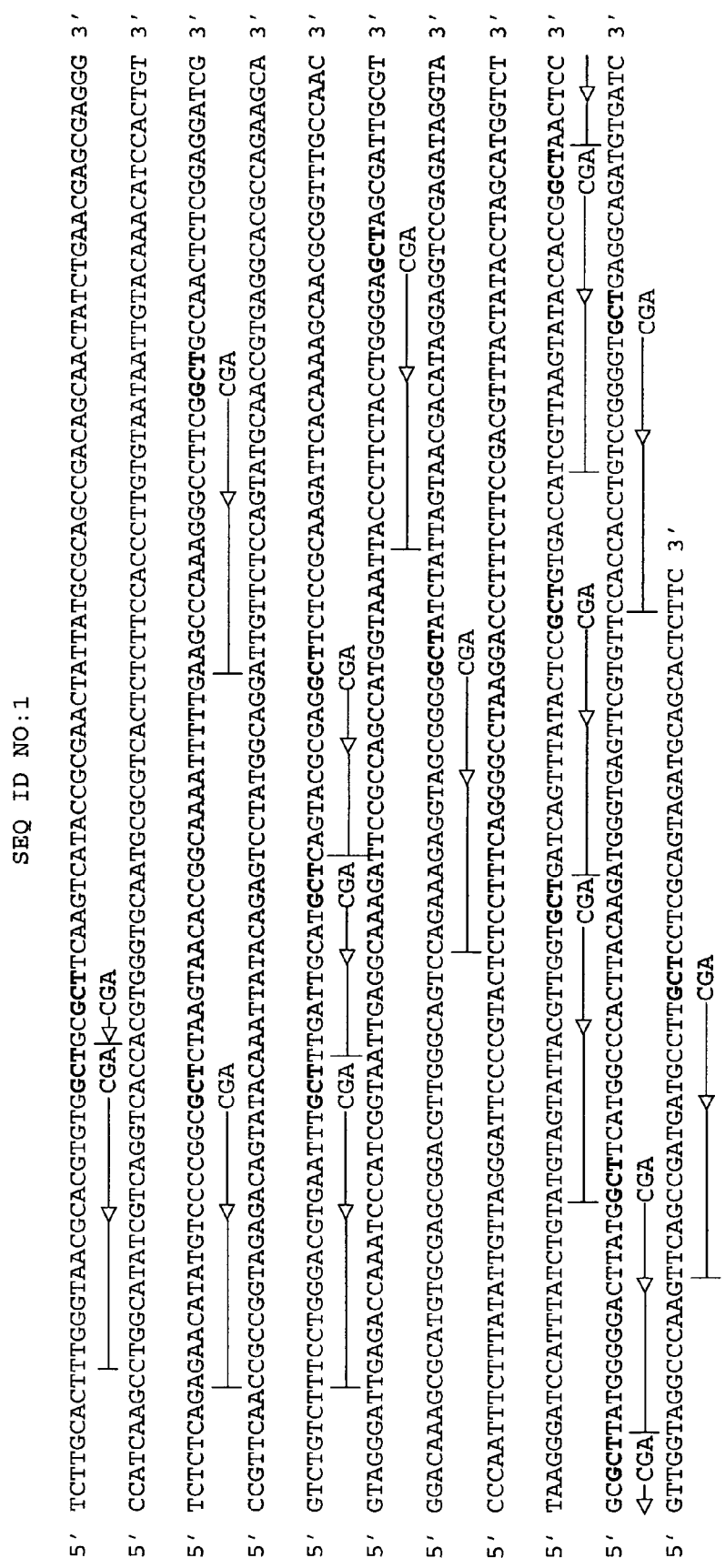
FIG. 3: The genomic DNA of FIG. 2 depicted denatured into two single-stranded genomic DNA templates, with the theoretical primer annealed to primer-binding sites on each of the denatured single-stranded genomic DNA templates, and arrows depicting elongation of SGP primer sequences over regions of each genomic DNA from which SGP nucleic acid polymers will be derived.

A representation of the first cycle of mPCR with the theoretical primer and genomic DNA sequences of Examples 1.1 and 1.2 is represented in FIGS. 3 and 4. FIG. 3 shows the theoretical genomic DNA sequence (also depicted in FIG. 2) as two denatured single-stranded DNA templates. The sequence of one of the single-stranded DNA templates is depicted 5'-to-3' and by uppercase letters (SEQ ID NO:1) in FIG. 3A, and the sequence of the complementary single-stranded DNA template is depicted 3'-to-5' and by lowercase letters (SEQ ID NO:2) in FIG. 3B. Also, bold letters indicate the expected primer annealing sites. The regions of the genomic DNA that the SGP nucleic acid polymers are expected to be derived from during the first cycle of amplification are represented underneath each genomic DNA template by 1) letters corresponding to the theoretical primer sequence underneath each primer-binding site to depict binding of the primer to the primer-binding site, 2) an arrow depicting the direction of elongation of the SGP nucleic acid polymer, and 3) a cross-hatch demonstrating the expected length of the elongated SGP nucleic acid polymer. Sequences of SGP nucleic acid polymers that are expected to be generated from each genomic DNA template after the first cycle of amplification are listed in FIG. 4. As shown, the sequences of some SGP nucleic acid polymers comprise SGP primer-binding sites (represented by bolded sequences).

During the denaturing step of the second and subsequent cycles of amplification, the SGP nucleic acid polymers having sequences comprising SGP primer-binding sites (as shown in FIG. 4) will be separated from each genomic DNA template, and will participate in subsequent annealing and elongation steps, i.e., they will not form higher-order structures. Consequently, in second and subsequent amplification cycles, in addition to the SGP nucleic acid polymers set forth in FIG. 4, a set of SGP-SGP nucleic acid polymers set forth in FIG. 5 will be synthesized and amplified.

One of skill in the art will readily recognize that each of the sequences set forth in FIG. 5, i.e., each SGP-SGP nucleic acid polymer sequence, is identical to one of the several regions of a genomic DNA template bracketed by primer-binding sites (as depicted with brackets in FIG. 2), i.e., is bracketed by the SGP primer sequence and the reverse complement of the SGP primer sequence. One of skill in the art will also recognize that subsequent cycles of amplification will result in an exponential doubling of the sequences listed in FIG. 5. It is approximated that after 22-24 cycles, approximately $10^6$ to $10^7$ copies of each distinct SGP-SGP nucleic acid polymer listed in FIG. 5 will be generated from one copy of the genome.

A "half-time" elongation step is included after several, e.g., 22-24, mPCR cycles containing full-time elongation steps, such that the 3'-end of some of the SGP-SGP nucleic acid polymers listed in FIG. 5 will not be copied because the elongation time is reduced. The "half-time" elongation step will be approximately 40-60% of the length of time used in the previous full-time elongation steps, for example, 50% of the length of time of the elongation step used above.

In this example, elongation during the half-time step occurs at ~72° C. for approximately 1 minute. Such a time for elongation allows the polymerization of 10 base pairs. As such, only a nucleic acid polymer derived from an SGP-SGP nucleic acid polymer that has one of the following sequences (as listed in FIG. 5) will be fully elongated such that it will comprise a primer-binding site: 3'-tcga-5' (set forth as SEQ ID NO:36), 3'-tcgccccga-5' (set forth as SEQ ID NO:37), 5'-AGCT-3' (set forth as SEQ ID NO:40), or 5'-AGCGGGGGCT-3' (set forth as SEQ ID NO:41). Such SGP-SGP nucleic acid polymers will not participate in the formation of higher-order structures.

In contrast, a nucleic acid polymer copied in a half-time elongation step from an SGP-SGP nucleic acid polymer having one of the following sequences (as listed in FIG. 5) will be a shortened SGP nucleic acid polymer, i.e., it will not have a sequence comprising a primer-binding site: 3'-tcgggtttcccg-gaagccga-5' (set forth as SEQ ID NO:35), 3'-tcggctactacg-gaacga-5' (set forth as SEQ ID NO:38), 5'-AGC-CCAAAGGGCCTTCGGCT-3' (set forth as SEQ ID NO:39), or 5'-AGCCGATGATGCCTTGCT-3' (set forth as SEQ ID NO:42). The sequences of SGP-SGP nucleic acid polymers and shortened SGP nucleic acid polymers expected to be derived from the SGP-SGP nucleic acid polymers listed in FIG. 5 after a half-time elongation step are listed in FIG. 6. The shortened SGP nucleic acid polymers, i.e., those that do not have an SGP primer-binding site and will participate in the formation of higher-order structures, are underlined in FIG. 6 and have sequences as follows: 5'-AGCCCAAAGG-3' (set forth as SEQ ID NO:43), 5'-AGCCGATGAT-3' (set forth as SEQ ID NO:46), 3'-cggaagccga-5' (set forth as SEQ ID NO:47) and 3'-tacggaacga-5' (set forth as SEQ ID NO:50).

The subsequent mPCR cycles including a half-time elongation step in place of the full-time elongation step result in single-stranded shortened SGP nucleic acid polymers that will not have complementary strands, thus they will form higher-order structures. These higher-order structures can be detected by performing Tm analysis (waveform profiling). In contrast, shorter SGP-SGP nucleic acid polymers, e.g., 5'-AGCT-3', will be completely elongated during mPCR with a half-time elongation step. Thus, because a complete complementary SGP-SGP nucleic acid polymer will always form during the half-time elongation step, these shorter SGP- SGP nucleic acid polymers will bind to their complementary nucleic acid polymer and will not participate in the formation of higher-order structures.

Example 2

Designing and Implementing SGP Primers

SGP primers were designed to generate distinct waveform profiles for genomic DNA obtained from ATCC (Manassas, Va.); the genomic DNAs tested were from the four closely related bacteria, *Escherichia coli* (ATCC #10798D), *Enterobacter cloacae* (ATCC #13047D), *Salmonella enterica* (ATCC #700720D), and *Providencia stuartii* (ATCC #33672D). Specific SGP primer sequences were selected by calculating the number of SGP primer-binding sites within the *E. coli* genome that would produce an SGP nucleic acid polymer.

Example 2.1

Designing SGP Primers

An SGP primer eight nucleotides in length was chosen for two reasons. First, if all four nucleotides (i.e., A, T, G, C) are used randomly to generate an SGP primer that is eight bases long, there are 65,536 possible sequence combinations. Therefore, it was reasoned that any SGP primer that is 8 bp would bind to its exact complementary sequence in one location every 65,536 bases. Second, the *E. coli* genome contains approximately 5 million bases, so an SGP primer eight base pairs in length would theoretically bind to 76 locations on the genome.

Additional constraints were defined to maximize elongation of SGP nucleic acid polymers and amplification of SGP-SGP nucleic acid polymers by a single SGP primer. For example, SGP primers were designed keeping in mind that distinct regions on the *E. coli* genome that are bracketed by SGP primer-binding sites should occur within 5,000 bases and be in the correct orientation to produce SGP-SGP nucleic acid polymers. For a potential SGP primer, the number of actual SGP primer-binding sites on the *E. coli* genome (set forth in GenBank with Accession No. U00096) was determined using the BLAST (Basic Local Alignment Search Tool) program provided by the NIH. The program reported the locations within the *E. coli* genome that were primer-binding sites. Primer design was also constrained by well-known parameters, e.g., preventing the formation of primer dimers by excluding any primer that may hybridize with itself.

Example 2.2

Implementing SGP Primers

Of 8 candidate SGP primers, two produced amplified SGP-SGP nucleic acid polymers with all four test bacteria. The sequences of the two primers are 5'-GCGAGGAT-3' (DJB7; set forth as SEQ ID NO:51) and 5'-GGCACTGC-3' (DJB8; set forth as SEQ ID NO:52). Blast results predicted that DJB7 would hybridize to the *E. coli* genome at 5 loci that have both the primer binding site and the reverse primer complement binding site within 5,000 bases, and DJB8 would hybridize to the *E. coli* genome at 10 such loci. Experiments using the DJB7 or the DJB8 primer compared the size and number of amplified SGP-SGP nucleic acid polymers under different reaction conditions via gel electrophoresis using 1% agarose gels stained with ethidium bromide. Initially, amplification (i.e., one or more cycles of denaturing, annealing, and elongating) was performed with 5 µM DJB8 primer (5'-GGCACTGC-3'), along with 1× Takara PCR buffer, 300 nM each dNTP, 2.5 mM MgCl$_2$, 2.5 units Takara polymerase (all available from Takara Mirus Bio, Madison, Wis.) and either 100 ng or 250 ng DNA. Thirty cycles of denaturing at 94° C. for 30 seconds, annealing at 25° C. for 30 seconds, and elongating at 72° C. for 30 seconds was performed to generate double-stranded SGP-SGP nucleic acid polymers from each of the four bacterial DNAs and from human DNA (as a control; Promega #G3041).

Waveform profiling using the above-described conditions, either DJB7 or DJB8, and different bacterial genomes resulted in amplified double-stranded SGP-SGP nucleic acid polymers of different sizes, i.e., a single pattern specific to each bacterial species (data not shown). Additionally, SGP-SGP nucleic acid polymer products amplified from human genomic DNA (Promega, Madison, Wis.) were undetectable when either primer was used (data not shown). The results demonstrate that an SGP primer can be applied to detect and distinguish among different bacterial DNAs, and also between bacterial DNA and human DNA.

Amplification of SGP-SGP nucleic acid polymers using one of the two SGP primers and bacterial DNA templates (including human genomic DNA as a control) was optimized. Several key parameters for successful amplification with an 8-base SGP primer were 1) a low annealing temperature, 2) a high concentration of primer, and 3) a high number of amplification cycles. Final optimal conditions were defined as 1× Takara PCR buffer, 300 nM each dNTP, 5.0 mM MgCl$_2$, 5.0 µM SGP primer, 2.5 units Takara Polymerase, and 1 ng template DNA; optimal cycling conditions were defined as 40 cycles of denaturing at 94° C. for 1 minute, annealing at 25° C. for 1 minute, and elongating at 72° C. for 1 minute.

Figure 7A:
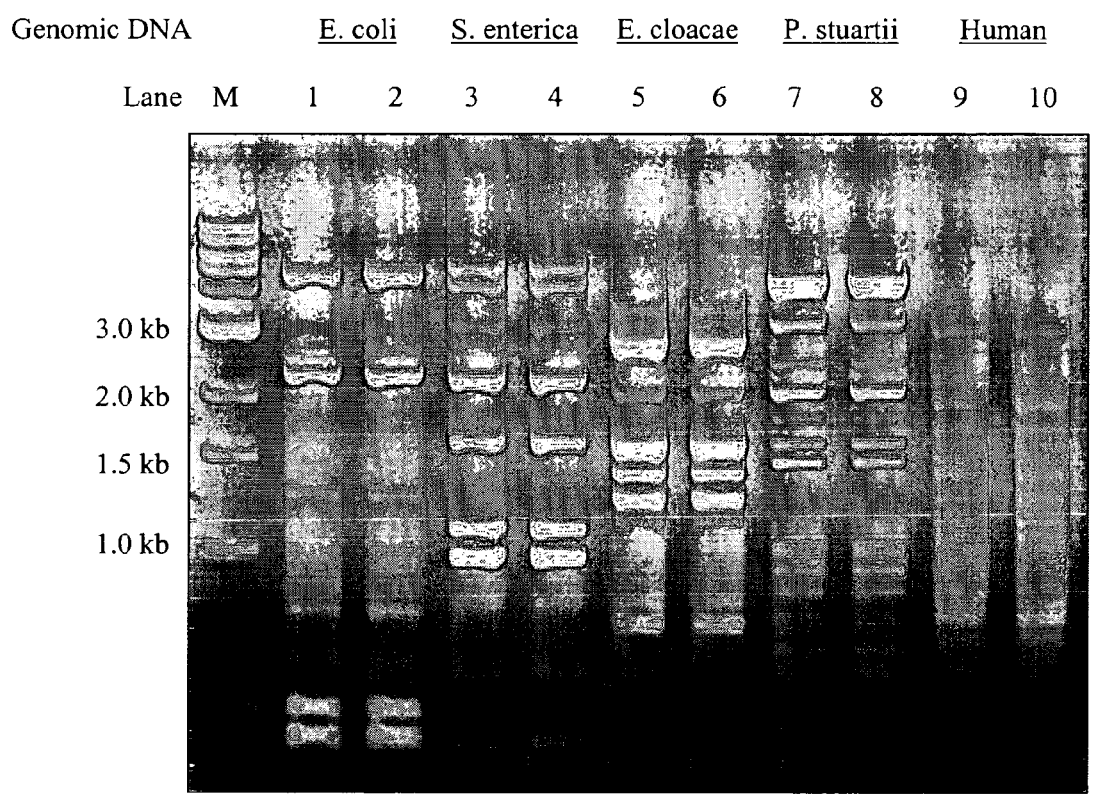
FIG. 7: Distinct patterns (lanes 1-10) of SGP-SGP nucleic acid polymers are produced for four different bacterial genomic DNA targets (lanes 1-8) and a human genomic DNA target (lanes 9 and 10) using either SGP primer DJB7 (FIG. 7A) or SGP primer DJB8 (FIG. 7B). A molecular weight ladder (lane M) shows the separation of select DNA molecules by size on a 1% agarose gel.
Figure 7B:
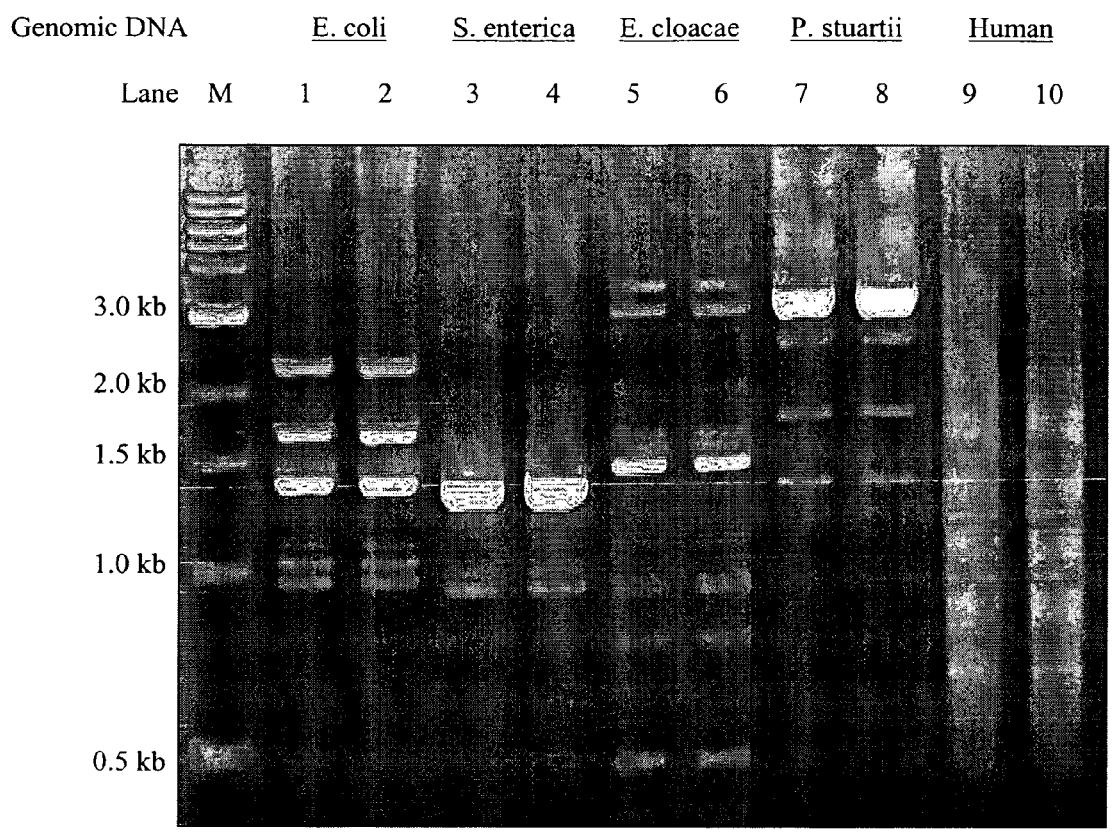

Amplification with either DJB7 or DJB8 (FIG. 7A and FIG. 7B, respectively) produced distinct patterns of double-stranded SGP-SGP nucleic acid polymers that can be used to distinguish different bacterial DNA from each another and/or bacterial DNA from human DNA. The data demonstrate that an SGP primer of the invention may be used in a waveform-profiling method of the invention to generate distinct patterns of amplified DNA, and that the detection of these distinct patterns may be used to detect and/or classify an organism even if the organism is present in a small amount.

The distinct patterns of double-stranded SGP-SGP nucleic acid polymers also may be detected by monitoring the change in fluorescence due to the release of an intercalating dye (e.g., SYBR® Green) in response to increasing temperature, i.e., the waveform profile generated using an SGP primer of the invention and an SGP method of the invention may be detected via melting temperature analysis. Additionally, a skilled artisan will recognize that a half-time elongation step may be incorporated such that the shortened SGP nucleic acid polymers resulting from the SGP-SGP nucleic acid polymers may form higher-order structures, which may also be detected via melting temperature analysis.

What is claimed is:

1. A method of exponentially amplifying DNA, the method comprising the steps of:
   (a) forming a polymerase chain reaction amplification mixture comprising the DNA, multiple copies of a single gene profiling (SGP) primer consisting of a primer sequence consisting of 6-9 nucleotides and other amplification reagents at appropriate concentrations, wherein the SGP primer binds to multiple sites on the DNA and functions as a forward primer and a reverse primer;
   (b) amplifying the DNA by a first polymerase chain reaction of the amplification mixture, wherein the first polymerase chain reaction comprises 10-100 cycles of denaturing, annealing and elongation steps to produce a first amplification product in the amplification mixture, wherein the elongation steps are performed for a first length of time, wherein the first amplification product comprises (i) first linear amplification products, wherein each of the first linear amplification products has a 5' end and a 3' end, contains the primer sequence at the 5' end, does not contain a reverse complement of the primer sequence at the 3' end and is single-stranded, and (ii) first exponential amplification products, wherein each of the first exponential amplification products has a 5' end and a 3' end, contains the primer sequence at the 5' end, contains a reverse complment of the primer sequence at the 3' end, and is double stranded, and wherein the first expontial products are produced during each cycle after the first cycyle of the first polmerase chain reaction; and (c) amplifying the first exponential amplification products by a second polymerase chain reaction of the amplification mixture, wherein the second polymerase chain reaction comprises one or more cycles of denaturing, annealing and elongation steps to produce a second amplification product in the amplification mixture, wherein the elongation steps are performed for a second length of time that is about 40%-60% of the first length of time, wherein the second amplification product comprises (i) second linear amplification products derived from a first portion of the first exponential amplification products, wherein each of the second linear amplification products has a 5' end and a 3' end, contains the primer sequence at the 5' end, does not contain a reverse complement of the primer sequence at the 3' end, is shorter in length than the first exponential amplification product from which it is derived and is single-stranded and (ii) second exponential amplification products derived from a second portion of the first exponential amplification products, wherein each of the second exponential amplification products has a 5' end and a 3' end, contains the primer sequence at the 5' end, contains a reverse complement of the primer sequence at the 3' end, is the same length as the first exponential amplification product from which it is derived and is double stranded and wherein the second exponential products are produced during each cycle after the first cycle of the second polymerase chain reaction, wherein the reverse complement of the primer sequence is fully complementary to the primer sequence.

2. The method of claim 1, which further comprises the step of:

(d) cooling the amplification mixture to form multiplexes of the second linear amplification products.

3. The method of claim 1, wherein the number of cycles in step (b) is 20-50.

4. The method of claim 3, wherein the number of cycles in step (b) is 30-40.

5. The method of claim 1, wherein the second length of time is about 50% of the first length of time.

6. The method of claim 1, wherein the number of cycles in step (c) is more than one.

7. The method as in either of claim 1 or claim 2, wherein the SGP primer has a nucleotide sequence selected from the group consisting of the nucleotide sequence set forth as SEQ ID NO:51 and the nucleotide sequence set forth as SEQ ID NO:52.

8. The method of claim 1, which further comprises the step of adding a detectable label. detecting at least one amplified product.

9. The method of claim 1, which further comprises the step of adding a detectable label.

10. The method of claim 9, wherein the step of detecting comprises performing melting temperature analysis.

11. A method of determining an organism in a sample comprising the steps of:

(a) acquiring the sample;
(b) extracting DNA from the sample;
(c) forming a polymerase chain reaction amplification mixture comprising the DNA, multiple copies of a single gene profiling (SGP) primer consisting of a primer sequence consisting of 6-9 nucleotides and other amplification reagents at appropriate concentrations, wherein the SGP primer binds to multiple sites on the DNA and functions as a forward primer and a reverse primer;

(d) amplifying the DNA by a first polymerase chain reaction of the amplification mixture, wherein the first polymerase chain reaction comprises 10-100 cycles of denaturing, annealing and elongation steps to produce a first amplification product in the amplification mixture, wherein the elongation steps are performed for a first length of time, wherein the first amplification product comprises (i) first linear amplification products, wherein each of the first linear amplification products has a 5' end and a 3' end, contains the primer sequence at the 5' end, does not contain a reverse complement of the primer sequence at the 3' end, and is single-stranded and (ii) first amplification products has a 5' end and a 3' end, contains the primer sequence at the 5' end,contains a reverse complement of the primer sequence at the 3' end and is double stranded,and wherein the first exponential products are produced during each cycle after the first cycle of the first polymerase chain reaction;

(e) amplifying the first exponential amplification products by a second polymerase chain reaction of the amplification mixture, wherein the second polymerase chain reaction comprises one or more cycles of denaturing, annealing and elongation steps to produce a second amplification product in the amplification mixture, wherein the elongation steps are performed for a second length of time that is about 40% 60% of the first length of time, wherein the second amplification product comprises (i) second linear amplification products derived from a first portion of the first exponential amplification products, wherein each of the second linear amplification products has a 5'% end and a 3' end, contains the primer sequence at the 5' end, does not contain a reverse complement of the primer sequence at the 3' end, is shorter in length than the first exponential amplification product from which it is derived and is single-stranded and (ii) second amplification products derived from a second portion of the first exponential amplification products, wherein each of the second exponential amplification products has a 5' end and a 3' end, contains the primer sequence at the 5' end, contains a reverse complement of the primer sequence at the 3' end, is the same length as the first exponential amplification product from which it is derived and is double stranded and wherein the second exponential products are produced during each cycle after the first cycle of the second polymerase chain reaction;

(f) cooling the amplification mixture to form multiplexes of the second linear amplification products; and (g) detecting the absence or presence of the multiplexes of the second linear amplification products, wherein the presence of the multiplexes determines the presence of an organism, wherein the reverse complement of the primer sequence is fully complementary to the primer sequence.

12. The method of claim 11, wherein the second length of time is about 50% of the first length of time.

13. The method of claim 11, wherein the number of cycles in step (d) is 20-50.

14. The method of claim 13, wherein the number of cycles in step (d) is 30-40.

15. The method of claim 11, wherein the number of cycles in step (c) is more than one.

16. The method of claim 11, wherein the temperatures for the elongation in steps (d) and (e) are the same temperature.

17. The method of claim 11, which further comprises the step of adding a detectable label.

18. The method of claim 17, wherein the step of detecting comprises performing melting temperature analysis.

19. The method of claim 11, wherein the SGP primer has a nucleotide sequence selected from the group consisting of the nucleotide sequence of SEQ ID NO:51 and the nucleotide sequence of SEQ ID NO:52.

* * * * *